US007645894B2

(12) United States Patent
Kanner

(10) Patent No.: US 7,645,894 B2
(45) Date of Patent: Jan. 12, 2010

(54) DIRECT PROCESS FOR MAKING CYCLIC DIMETHYLSILOXANE OLIGOMERS

(75) Inventor: Bernard Kanner, West Nyack, NY (US)

(73) Assignees: Bernard Kanner, West Nyack, NY (US); George A. Skoler, White Plains, NY (US)

(*) Notice: Subject to any disclaimer, the term of this patent is extended or adjusted under 35 U.S.C. 154(b) by 172 days.

(21) Appl. No.: 11/649,193

(22) Filed: Jan. 3, 2007

(65) Prior Publication Data

US 2007/0249855 A1 Oct. 25, 2007

Related U.S. Application Data

(63) Continuation-in-part of application No. 11/409,359, filed on Apr. 22, 2006, now abandoned, and a continuation-in-part of application No. 11/446,478, filed on Jun. 2, 2006, now abandoned.

(51) Int. Cl.
*C07F 7/04* (2006.01)
(52) U.S. Cl. ...................................................... 556/473
(58) Field of Classification Search .................. 556/473
See application file for complete search history.

(56) References Cited

U.S. PATENT DOCUMENTS

| 2,380,996 | A | | 8/1945 | Rochow et al. |
|---|---|---|---|---|
| 2,443,902 | A | | 6/1948 | Ferguson et al. |
| 2,464,033 | A | | 3/1949 | Gilliam |
| 2,563,557 | A | | 8/1951 | Schubert et al. |
| 3,641,077 | A | | 2/1972 | Rochow |
| 3,775,457 | A | | 11/1973 | Muraoka et al. |
| 4,088,669 | A | * | 5/1978 | Malek et al. ................ 556/472 |
| 4,500,724 | A | | 2/1985 | Ward et al. |
| 4,593,114 | A | * | 6/1986 | Lewis et al. ................ 556/450 |
| 4,727,173 | A | | 2/1988 | Mendicino |
| 4,761,492 | A | | 8/1988 | Childress et al. |
| 4,762,940 | A | | 8/1988 | Halm et al. |
| 4,864,044 | A | | 9/1989 | Lewis et al. |
| 4,898,960 | A | | 2/1990 | Dosaj et al. |
| 4,999,446 | A | | 3/1991 | Moody et al. |
| 5,084,590 | A | | 1/1992 | Ritscher et al. |
| 5,166,384 | A | | 11/1992 | Bailey et al. |
| 5,527,937 | A | | 6/1996 | Standke et al. |
| 5,783,720 | A | | 7/1998 | Mendicino et al. |
| 6,258,970 | B1 | | 7/2001 | Ward et al. |
| 6,380,414 | B2 | | 4/2002 | Brand |
| 6,580,000 | B1 | | 6/2003 | Anderson et al. |
| 6,727,375 | B2 | | 4/2004 | Steding et al. |

FOREIGN PATENT DOCUMENTS

WO PCT/US01/43581 11/2001

OTHER PUBLICATIONS

C. Eaborn, "Organosilicon Compounds," 1960, title page, p. 231, Butterworths Scientific Publications, London, U.K.

Walter Noll, "Chemistry and Technology of Silicones," 1968, title page, back of title page, pp. 192-195, 197, Academic Press, New York, NY.
Dietmar Seyferth, "Dimethyldichlorosilane and the Direct Synthesis of Methylchlorosilanes. The Key to the Silicones Industry," Organometallics, 2001, 20 (24), 4978-4992, web release date: Nov. 19, 2001.
R.J.H. Voorhoeve, "Organohalosilanes," 1967, title page, back of title page, pp. 120-123, 127, 139-140, 143-145, Elsevier Publishing Company, New York, NY.
K.M. Lewis, D.G. Rethwisch, Ed. "Catalyzed Direct Reactions of Silicon," 1993, cover, title page, back of title page, table of contents, pp. vii, viii, preface by E. G. Rochow, pp. xiii, xiv, Elsevier Publishing Company, New York, NY.
B. Kanner, K. M. Lewis, "Commerical Production of Silanes by the Direct Process 1993, pp. 1-66," Catalyzed Direct Reactions of Silicon, Lewis, Rethwisch, Ed. Elsevier Publishing Company, New York, NY.
K.M. Lewis, et al., "Selection of Copper Formate Catalysts for the Direct Synthesis, of Methylchlorosilanes," 1993, pp. 117-155, "Catalyzed Direct Reactions of Silicon," Lewis, Rethwisch, Ed., Elsevier Publishing Company, New York, NY.
B. Pachaly, et al., From Waste to Valuable Products: Work Up of Silicon Metal ByProducts From the Direct Process, 1994, pp. 235-239, Silicon for the Chemical Industry II, The Norwegian University of Science and Technology, Trondheim, Norway.
C.S. Kuivila, et al., The Control of the Methylchlorosilane Product Distribution From the Rochow Direct Process, 1996, pp. 227-238, cover page, title page, table of contents, Silicon for the Chemical Industry III, Norwegian U. Sc. & Tech.
L.N. Lewis, et al., "Surface Analysis of MCS Beds," 1998, p. 157, cover and title pages, Silicon for the Chemical Industry IV, The Norwegian University of Science and Technology, Trondheim, Norway.
K.M. Lewis, et al., "Solvent Remediation and Reuse in the Direct Synthesis of Trimethoxysilane," pp. 151-161, 164-167, Silicon for the Chemical Industry V, The Norwegian University of Science and Technology, Trondheim, Norway.
W.J. Ward, et al., "Exploring the Effects of Phosphorus in the Direct Process with a Fixed Bed Reactor," 2000, pp. 309-319,324, cover& title pgs, Silicon for the Chemical Industry V, The Norwegian University of Science and Technology, Trondheim, Norway.
Rösch, Some Perspectives in Silicones Chemistry, 2002, pp. 13-21, Silicon for the Chemical Industry VI, The Norwegian University of Science and Technology, Trondheim, Norway.

(Continued)

Primary Examiner—Daniel M Sullivan
Assistant Examiner—Chukwuma O Nwaonicha
(74) Attorney, Agent, or Firm—George A. Skoler

(57) ABSTRACT

The invention relates to continuous processes for making cyclic dimethylsiloxane oligomers by reacting in situ methyl bromide, dimethyl ether and activated silicon particles in a direct process reaction zone to produce methylsiloxanes, wherein the proportion of dimethylsiloxane produced in said reaction zone is greater than 75 mole % of the methylsiloxanes produced and recovering the dimethylsiloxane from the reactions zone. The invention favors making cyclic dimethylsiloxane oligomers by this in situ direct reaction.

25 Claims, 2 Drawing Sheets

OTHER PUBLICATIONS

J.G.R. Poço, et al., "The effect of Ca, Al, and Fe in the direct synthesis of dimethyldichlorosilane from undoped Si 99,999%," 2002, pp. 169-174, Silicon for the Chemical Industry VI, The Norwegian Univ. Science & Techn., Trondheim, Norway.

H.W. Kim, et al., "The effects of promoters in the Direct Process for methylchlorosilane," 2002, pp. 175-181, Silicon for the Chemical Industry VI, The Norwegian University of Science and Technology, Trondheim, Norway.

K.M. Lewis, et al., "Direct reactions of silicon with nanosized copper and copper compounds as catalyst precursors," 2002, pp. 243-263, Silicon for the Chemical Industry VI, The Norwegian University of Science and Technology, Trondheim, Norway.

* cited by examiner

"Solvent Slurry Process"

"Fluid Bed Process"

DIRECT PROCESS FOR MAKING CYCLIC DIMETHYLSILOXANE OLIGOMERS

RELATED PATENT APPLICATION

This application is a continuation-in-part of U.S. application Ser. No. 11/409,359, filed Apr. 22, 2006, commonly assigned, and U.S. application Ser. No. 11/446,478, filed Jun. 2, 2006, commonly assigned.

BRIEF DESCRIPTION OF THE INVENTION

This invention relates to a novel continuous process for making dimethylsiloxane directly by the reaction at an elevated temperature of a mixture of methyl bromide and dimethyl ether within a dynamic bed of thermally activated silicon metal particles associated with copper catalyst and promoter, agitated by gas fluidization or stirring in the form of a slurry in an inert liquid solvent, such that there is at least one complete silicon metal bed turnover during the continuous process and the proportion of dimethylsiloxane produced in said bed is greater than 75 mole % of the methylsiloxanes produced from said reaction. In particular, this invention encompasses a process for making cyclic dimethylsiloxane oligomers by continuously feeding dimethyl ether and methyl bromide into stirred inert liquid containing an agitated suspension of direct synthesis quality particulate silicon metal associated with direct synthesis quality promoted copper catalyst, thereby enhancing the production of cyclic dimethylsiloxane oligomers in said liquid suspension. In addition, this invention relates to a solvent composition derived from a process which relates to an in situ direct reaction process product mixture within a direct process reaction zone which is predominantly cyclic dimethylsiloxane oligomers.

BACKGROUND OF THE INVENTION

Generically, the direct synthesis or process or aka "the Rochow direct process or synthesis" is recognized to include the reactions of promoted silicon with hydrogen halides, alkyl halides, alcohols, and dimethylamine. Alcohols and alkyl ethers may be used in combination with hydrogen halides and alkyl halides. The direct synthesis is the principal process for commercially making organosilicon compounds. However, alkyl ethers with or without alkyl halides have not been employed in any commercial process for making alkylsilanes and alkylsiloxanes. The commercial processes involve the exothermic reaction of methyl chloride or methanol with copper catalyzed particulate activated silicon. In the first stage of the reaction, they produce the methylchlorosilanes in the case of the methyl chloride reaction or methoxysilanes in the case of the methanol reaction. Catalyzation of the reaction with silicon is achieved in these commercial processes using copper per se or copper compounds. However, the art teaches that silver or silver compounds may be used as the catalyst. In its preferred and most commercial embodiment, the Rochow direct process involves the reaction of methyl chloride within a fluidized bed of activated silicon that is catalyzed by copper with additional promoters, such as aluminum, tin, zinc, phosphorus, and the like, including compounds containing such elements. (See, Rochow, CHEMISTRY of the SILICONES, second edition, pages 36-41[1], John Wiley and Sons, Inc., New York, N.Y., 1951 and Noll, Chemistry and Technology of Silicones, 1968, published by Academic Press, New York, N.Y., starting at page 26.[2]).

[1] Incorporated by reference.
[2] Pages 26 through 41 of Noll, infra, are incorporated herein by reference. (Specific reference is made to footnotes 200-209 of Noll, cited at page 65)

According to Rochow (page 36 supra):

"There are several widely different methods for the synthesis of organosilicon compounds that have but one feature in common: they do not require other organometallic compounds as reagents, nor do they employ stoichiometric quantities of active metals for the preparation of such organometallic reagents in situ. The first of these methods to be considered employs elementary silicon as the source of that element; the others employ the reaction of hydrocarbons with suitable compounds of silicon."

Illustrative of the variety of chlorosilanes produced in the first stage of the Rochow direct synthesis, reference is made to Ward, et al., "EXPLORING THE EFFECTS OF PHOSPHORUS IN THE DIRECT PROCESS WITH A FIXED BED REACTOR," at page 309 of *Silicon for the Chemical Industry V*, Tromso, Norway, May 29-Jun. 2, 2000, Trondheim, Norway 2000 published by Norwegian University of Science and Technology, Trondheim, Norway), which they characterize as follows:

I.

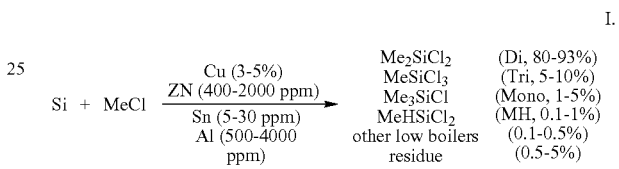

"Me" stands for the methyl group

The commercial methylsilicones are made by the hydrolysis of methylchlorosilanes generated by the Rochow fluidized bed process and the condensation of the hydrolyzate into methylsiloxanes (methyl silicones). Of the methyl silicones, dimethyl silicones are the most widely utilized. Consequently, there is a strong preference for increasing the yield of and selectivity to dimethyldichlorosilane in the direct process. According to Rochow (page 38 supra): "The direct synthesis . . . it is best suited to the preparation of dialkyl- or diaryldihalosilanes, and the operation of the reaction is more satisfactory if limited further to the chlorosilanes and bromosilanes." Dialkylsilicon esters (e.g., alkoxides) are not made commercially by the direct process. As noted from the first stage (I) equation, byproduct silicon chlorides are inevitably formed in carrying out the direct synthesis. Because the direct synthesis is commercially carried out as a fluid bed process, the typical issues of fluid bed fines and disilanes as well as coking[3] within the bed (inducing bed agglomeration) represent significant first stage processing problems. Essentially all of these byproducts and bed contamination represent environmentally hazardous and corrosive materials and their presence adds materially to the cost of making the dimethyldichlorosilane.

[3] See The Lewis Report's reference to the work of Kim and Rethwisch, infra.

Whereas the commercial processes that are employed to make alkyl-silicon halides, particularly methyl and ethyl silicon halides, are typically carried out in a gas/vapor dynamic particulate fluidized or stirred bed of promoted silicon metal particles; the methoxysilanes, such as tetramethylsilicate, trimethoxysilane, and dimethoxysilane, are formed by the direct reaction of alcohol with silicon slurried in an inert liquid. Trimethoxysilane is commercially made in Italy by the reaction of methanol with silicon slurried in an inert liquid. These processes are discussed in greater detail below. Such methoxysilanes can be made by the non-direct process reaction of a chlorosilane with methanol.

The Direct Synthesis to Produce Alkylsilicon Compounds

There are many applications where silicones could be an obvious choice but are not considered because of their high cost, thus impairing new product development. Consequently, there is a desire by the industry to make the products of the direct process cheaper, see L. Rösch, "Some Perspectives in Silicones Chemistry," Silicon for the Chemical Industry VI, Loen, Norway, Jun. 17-21, 2002, Trondheim, Norway, 2002 (published by Norwegian University of Science and Technology, Trondheim, Norway).

One of the significant reasons for the high cost of dimethyldichlorosilane and dimethylsilicones is the high capital cost of an industrial dimethyldichlorosilane and dimethylsilicones plant, and in particular, in the cost of the distillation facilities therein to separate out the desired chlorosilane products, the cost in dealing with byproduct HCl, the cost in recovering chlorine values from the hydrolysis of the chlorosilanes, and the cost of hydrolysis and condensation to make dimethylsilicone oligomers for the general manufacture of the various silicone products being currently sold or used. Any direct reaction process that produces a mixture of methylchlorosilanes is going to suffer from these issues.

According to Kanner and Lewis, "Commercial Production of Silanes by the Direct Synthesis", at pages 1-66, specifically at page 23, published in K. M. Lewis and D. G. Rethwisch (Eds.), *Catalyzed Direct Reactions of Silicon*, by Elsevier Science Publishers B. V. 1993:

"Distillation columns and their ancillary equipment probably account for about half of the capital cost of a Direct Synthesis plant. The product mixture to be separated and refined consists of many closely boiling compounds (see Table 6), some of which form azeotropic mixtures. Moreover, the refined products have stringent purity requirements related in their end use. For example, dimethyldichlorosilane must contain less than 0.05 wt % methyltrichlorosilane to satisfy premium grade elastomer specifications. The principal monomers, methyldichlorosilane, trimethylchlorosilane, methyltrichlorosilane and dimethyldichlorosilane, are isolated by continuous fractionation in multiplate columns."

The complexity of the distillation problem associated with the commercial direct synthesis process can be gleaned from a "partial list" of 30 products reported in Table 7 of Kanner and Lewis, "Commercial Production of Silanes by the Direct Synthesis," supra, at page 27, which are present in the product to be distilled.

According to Schubert, et al., U.S. Pat. No. 2,563,557, the crude mixture obtained from the direct synthesis in which methyl chloride is passed over heated silicon yields a designated six fractions. They point out from the data in Table 1 (column 1 of the patent)—"that there is a slight gradient in boiling points of trimethylchlorosilane, methyltrichlorosilane, dimethyldichlorosilane, and silicon tetrachloride. Because of these small differences in boiling points, especially between silicon tetrachloride and trimethylchlorosilane, and methyltrichlorosilane and dimethyldichlorosilane, great difficulty has been experienced in separating the different components." According to a Dow Corning internet publication ("Silicones: Preparation, Properties and Performance," by André Colas, Dow Corning, Life Sciences): "The various silanes are separated by distillation: as the boiling points are close together, long distillation columns are always seen at silicone factories." (See page 4 of the Dow Corning publication[4]) According to Silicones Science On-Line:[5] "Due to the sometimes very small differences between the boiling points of silanes (e.g., methyltrichlorosilane at 66° C., dimethyldichlorosilane at 70° C.) distillation units have to fractionate them in several stages to obtain the individual silanes. The distillation columns therefore have many plates and thus high separation efficiency. Even small amounts of contaminants (e.g. $CH_3SiCl_3$ in $(CH_3)_2SiCl_2$), in the parts per million (ppm) range, interfere with the further processing of the organochlorosilanes to silicones."

[4] http://www.dowcorning.com/content/publishedlit/01-3077.pdf?DCWS=Food%20and%20Beverage&DCWSS=

[5] See: http://www.silicones-science.com/chemistry_silanes.html

Thus, the second stage of the Rochow direct process is the distillation step, viz.,

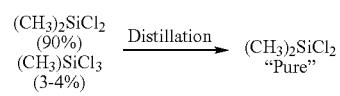

II.

The third stage of the Rochow direct process is the hydrolysis of the dimethyldichlorosilane to produce dimethylsiloxane oligomers, e.g.,

III.

This stage of the process necessitates the use of costly corrosion resistant equipment and adds a fourth stage to the process to recover the chlorine values. As much as 5 wt % of the HCl can be lost to neutralization and disposal in landfills. One or both of the following two reaction steps are employed in the cyclic direct process in order to recover the chlorine:

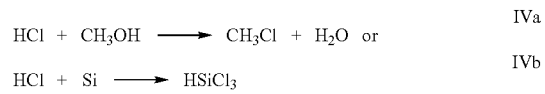

Direct Process Residues from the Rochow Direct Synthesis can represent from "4% to 8% of the total raw material cost for dimethyldichlorosilane."[6] Significant investment or high processing costs are involved in dealing with that issue.

[6] Brinson, Recovery of Valuable Chlorosilane Intermediates by a Novel Waste Conversion Process, DOE/AL/99566-4, December 2001, for U.S. Department of Energy by Dow Corning Corporation. http://www.osti.gov/bridge/servlets/purl/795522-82wKri/webviewable/795522.pdf Stage IVa requires the addition of another reactant, methanol, and stage IVb generates the less desirable trichlorosilane rather than the more desirable dimethyldichlorosilane, the primary product of the Rochow direct process.

The typical fifth stage of the Rochow direct process involves the conversion of the linear dimethylsiloxane condensates to cyclic dimethylsiloxane oligomer, viz.,

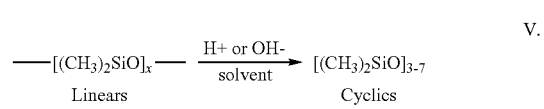

V.

Considering that plants for a facility[7] to effect the direct process can cost about $300 million up to about $1 billion,[8] it is obvious any process that minimizes distillation and corrosion issues and eliminates a number of process steps—the more the better—associated with the current commercial Rochow direct process as well as the costs incurred in treating Direct Process Residues including HCl, will materially impact and add value to the silicones industry.

[7] "Today European manufacturers no longer consider as commercially viable plants producing less than 60,000 tones per year." Silicones Science On-Line, http://www.silicones-science.com/chemistry_silanes.html

[8] See: Matisons, "Alternatives to the Direct Process in Producing Silicon Materials," *Silicon for the Chemical Industry VII*, M S Trolifjord, Tromsø-Bergen, Norway, Sep. 21-24, 2004, Trondheim, Norway, 2004, who states: "Plant costs to produce such materials can approach one billion dollars (depending on the scale of the operation), and inevitably the cost of any silicon materials is high (e.g. compared with organic polymers)."

According to Noll, at page 29 supra,

"In the past, no other aspect of the direct synthesis has received so much attention and effort as the search for suitable catalysts. It is difficult, if not impossible, for the uninitiated to extract from the sometimes contradictory evidence in the literature a generally valid guide for the best method of working. The value of a large part of this work is limited by the fact that attention has been concentrated exclusively on the problem of catalysts, without at the same time considering the large number of other factors which also have a bearing on the result. At least, it is impermissible to compare the results of different authors directly for this reason."

Though the direct synthesis is predicated to a significant extent on empirically derived information, it has been explored by those having ordinary skill in the art for many years and has been advanced substantially since Noll was published [1968]; and as the art has gained maturity there is now a significant body of art that can be relied on by those having ordinary skill in the art, which makes the direct synthesis routine to them to achieve a desired reaction product without regard to optimization, and provides those having ordinary skill in the art to possess the intellectual resources to comprehend new advances in the direct synthesis and the capacity to employ them. However, one having ordinary skill in the art is a highly skilled scientist, e.g., one having an advanced degree, desirably a PhD in chemistry or chemical engineering, working knowledge and comprehension of this large body of direct synthesis art information, and extensive experience (typically, at least three years experience) in research and/or industry directed to exploring the direct synthesis.

The Prior Art's Efforts at Non-Halogen Based Systems for Making Organosilicones by the Direct Reaction In a Technical Report by Dr. Larry N. Lewis, entitled "Recent Advances in the Direct Process," dated August 1996, from the GE Research & Development Center,[9] (see *The Chemistry of Organic Silicon Compounds*, Volume 2, Parts 1, 2, &3, Zvi Rappoport (Editor), Yitzhak Apeloig (Editor), September 1998), (hereinafter called "The Lewis Report") Dr. Lewis discusses alternative methods to formation of Si—$CH_3$ bonds:

Newton and Rochow reported low (1-2%) yields of methylalkoxysilanes during the copper catalyzed reaction of his silicon and methanol [W. E. Newton, E. G. Rochow, *Inorg. Chem.*, 9, 1071 (1970)]. In 1988 a group from Lopata R&D Corporation reported a version of the silicon methanol direct reaction wherein they added metal formates such as potassium formate . . . . Rochow has stated that non-halogen based direct process was and continues to be one of the great challenges left for silicon direct process [E. G. Rochow, *Main Group Chemistry News*, 2, 27 (1995)] . . . .

Two groups have made minor breakthroughs in non-halogen direct process. In 1978 Malek and Speier reported the reaction between dimethyl ether and silicon [U.S. Pat. No. 4,088,669] . . . . While this process was not entirely halogen free, it was the most successful ether silicon direct process to date.

Since the Malek and Speier work, Lewis and Kanner also reported a dimethyl ether direct process which was a great improvement over Malek's and Speier's [sic] because it employed a fluidized bed in place of an autoclave [U.S. Pat. No. 4,593,114 and European Patent Application EP 175282 (1986), CA 105: 60,753]

[9] See http//192.35.44.9/cooltechnologies/pdf/1996crd106.pdf

Direct Reaction Involving Dimethyl Ether, Methyl Bromide and Silicon

Malek, et al., in the aforementioned U.S. Pat. No. 4,088,669, describe the reaction of dimethyl ether and catalytic amounts [see col. 5, line 19-25] of methyl bromide with activated silicon under non-continuous closed autogenous conditions to produce dimethyldimethoxysilane.

The residence times mentioned in the patent measured in many hours because the conditions of the autogenous reaction seemingly precluded high reaction rates. Though this patent makes reference to the manufacture of siloxanes, all such references are to the generic concept of making alkoxy substituted siloxanes. The patent is specifically oriented to the manufacture of alkoxy-substituted silanes and siloxanes. This point is emphasized at column 5, lines 1-5 wherein Malek, et al. point out that the hydrolyzable nature of the silicon-alkoxy bond which is inherent in the products of the reaction requires avoiding "more than trace amounts of water in the reaction mixture." Further emphasis of alkoxy formation is given at column 5, lines 32-35, wherein the patentees state:

"The organosilicon products of the method of this invention bear . . . at least one silicon-bonded hydrocarbonoxy radical per molecule."

Malek, et al., at column 4, lines 37-40, indicate that "an inert liquid" may be used during the autogenous reaction.[10] In Example 2 of the patent, the autogenous reaction involving dimethyl ether and catalytic amount of methyl bromide was repeated with decalin added and the equivalent percents of methyl silicon and silicon methoxide increased. In example 5, table II reports the results of three experiments labeled 5-1, 5-2, and 5-3, in which the reaction conditions were varied. Using methyl chloride, with experiment 5-1 as the base case, experiment 5-2 shows that by increasing the dimethyl ether to silicon ratio there is an essentially commensurate increase in the manufacture of trimethylmethoxysilane and dimethyldimethoxysilane, and a much greater increase in the manufacture of methyltrimethoxysilane. In the same two experiments, the varied conditions resulted in a different mix of methoxy-substituted siloxanes. On the other hand, experiment 5-3 employs incrementally higher dimethyl ether to silicon ratio and uses a small methyl bromide to silicon ratio: in addition, the experiment employs a small amount of mineral oil. The results for this experiment indicate only a large equivalent percent of dimethyldimethoxysilane. Thus, the most that can be gleaned from example 5-3 is that by including methyl bromide in the reaction the formation of dimethyldimethoxysilane was materially increased. Example 9 (with the exception of experiment 9-4) of Malek, et al., describes the autogenous reaction of "activated silicon alloys" in the presence of dimethyl ether and methyl bromide using decalin, which is presumed to be an inert liquid in the autogenous reaction. All of the autogenous reactions were carried out for a period of at least 15 hours. Example 10 of Malek, et al. reports the results of a similar set of experiments in TABLE VII, in which the autogenous reactions were all carried out for 16 hours.

[10] It should be noted that the Technical Report by Dr. Larry N. Lewis, supra, fails to note Malek, et al.'s employment of "inert liquid."

Lewis and Kanner,[11] U.S. Pat. No. 4,593,114, patented Jun. 3, 1986, mentioned in the Technical Report by Dr. Larry N. Lewis, describe a process for preparing cyclic and oligomeric organosiloxanes by reacting hydrocarbon ether and a hydrocarbon halide within a fluidized or agitated bed of activated silicon particles at a maximum contact time of five minutes and continuously withdrawing products from the reaction. According to the patent, at column 1, lines 21 et seq., "the direct synthesis of the dimethylsiloxanes from dimethyl ether and suitably activated silicon has been of interest for many years. This has been so because a successful synthesis would reduce the cost and complexity associated with the state-of-the-art process." The patent points out that a mixture of methylchlorosilanes is made by the direct synthesis, and the mixture is separated by multiplate distillation to obtain high purity dimethyldichlorosilane, which is subsequently hydrolyzed to cyclic and linear dimethylsiloxanes. Later in the column, the patent discusses corrosion, pollution, rate and selectivity problems with respect to liberated HCl. "It is to obviate these complexities that there has been much interest in obtaining the direct synthesis of dimethylsiloxanes from silicon and dimethyl ether."[12]

[11] Dr. Kanner is the inventor of the instant application.
[12] The state of the prior art is further amplified in the Lewis and Kanner patent, and such is incorporated herein by reference, especially the discussion at column 2 to column 3, line 41.

Malek, et al. and Lewis and Kanner address Yamada, et al., Japanese Patent 187,342. According to Malek, et al., at column 1, 43-47, Yamada, et al. describe "the reaction of alkyl and aryl ethers with metallic silicon and atmospheric pressure in a flow-through, hot tube system to produce alkylalkoxysilanes and arylalkoxysilanes." Malek, et al. indicate that the Yamada, et al. process was not adopted for commercial production "in spite of its attractiveness." Malek, et al. suggest that this non-adoption may be due to the work of Zuckerman who in a 1960 Ph.D. thesis "concluded that the reaction of ethers with silicon as stated by Yamada, et al. does not produce organosilicon compounds." Malek, et al. further state that Newton, et al., *Inorg. Chem.*, 9, 1072 (1971) "failed to produce methylmethoxysilanes from the reaction of dimethyl ether with a silicon-copper alloy in a silicone oil slurry."

Lewis and Kanner emphasize at column 3, lines 33-41, that the use of solvents in the direct synthesis process is undesirable, to wit, "While the use of an inert solvent, as specified in U.S. Pat. No. 4,088,669, reduces the heat and mass transfer problems, said solvent must be free of impurities which inhibit the synthesis of dimethyldimethoxysilane. Recycle of the solvent is essential for the economic practice of this synthesis. Hence additional processing steps (e.g., filtration and distillation) which add to the complexity of the synthesis are required."

No benefits other than reducing heat and mass transfer problems by the use of an inert solvent are appreciated by Lewis and Kanner, and those benefits were not seen to outweigh the "additional processing steps." However, it must be appreciated that Lewis and Kanner were solely concerned with effecting the process in a fluidized bed, and solvent usage in that kind of system obviously made little sense to them. Consequently, the use of inert solvent was rejected by Lewis and Kanner.

Many years later, Dr. K. M. Lewis, of the above patent, working independently of Dr. Kanner, published an article in 2002 with others [K. M. Lewis, et al., "Direct reactions of silicon with nanosized copper and copper compounds as catalyst precursors," Silicon for the Chemical Industry VI, pages 243-263, Loen, Norway, Jun. 17-21, 2002, Norwegian University of Science and Technology, Trondheim, Norway], in which they describe the general applicability of the use of solvent in carrying out the Rochow direct process, and survey the prior art for early experiments showing the kinship between the conditions of running methyl chloride and alcohol within a (in this case a nanosized) copper catalyzed particulate silicon metal suspension to effect a Rochow direct process: the regimens cited in the article are incorporated herein by reference. According to this article and the prior art cited therein, the direct synthesis to react methyl chloride with copper catalyzed silicon particles suspended in a solvent results in the efficient formation of dimethyldichlorosilane, much in the manner that it is formed by the fluidized bed process. Though Dr. K. M. Lewis is aware of the suitability of using a solvent in the direct process in making methylchlorosilanes, he did not carry out any experiments involving the use of solvents, dimethyl ether and methyl halide and no reactions involving methyl bromide. However, all of the stages I-V problems cited above for the commercial fluidized bed Rochow process are equally applicable with respect to the production of methylchlorosilanes in a solvent slurry with the exception of the coking and agglomeration issues and the loss of silicon fines via elutriation, cited previously. See also Lewis, et al., PCT/US01/43581 (WO 02/44186) based on U.S. Provisional Patent Application Ser. No. 60/250,915, filed Dec. 1, 2000.

Lewis and Kanner's Example 5 (columns 11 and 12) describes the reaction of methyl bromide and dimethyl ether in the presence of activated silicon "to yield a higher content of siloxanes than was realized with $CH_3Cl$ and $(CH_3)_2O$ under analogous reaction conditions." In section (a) of example 5, all of the products formed were bromosilanes. No dimethyl ether was employed in that experiment even though the first paragraph of the example states, "This Example shows that $CH_3Br$ and $(CH_3)_2O$ react with activated silicon . . . ." In section (b) of Example 5, methyl bromide gas and dimethyl ether were reacted in the presence of the promoted silicon metal fluidized bed of section (a) to form the following mixture of silanes and siloxanes, as determined by gas-chromatographic/mass spectrometric analysis (see column 12, lines 7-10):

| $(CH_3)_3SiOCH_3$ | $(CH_3)_3Si[OSi(CH_3)_2]_nOCH_3$ | n = 1, 2, 3 and 4 |
|---|---|---|
| $(CH_3)_3SiOSi(CH_3)_3$ | $(CH_3)_3Si[OSi(CH_3)_2]_nOSi(CH_3)_3$ | n = 1, 2, 3 and 4 |
| $(CH_3)_2Si(OCH_3)_2$ | $[(CH_3)_2SiO]_n$ | n = 3, 4, 5, 6 and 7 |

According to Example 5(b), "the total content of siloxanes in the product was 83.58 wt %. Less than 1% of dimethyldimethoxysilane was formed." Example 4 of the patent describes the reaction of dimethyl ether and methyl chloride in the fluidized bed reaction and the "total content of linear, cyclic and functionalized siloxanes was 8.09 wt %." There is no data as to the amount of any of the siloxanes in either example.

It is to be noted that while the trimethyl endblocker is evident in some of the products obtained in said Example 5(b), no products containing tri-functional siloxane units, e.g., $CH_3SiO_{1.5}$, are identified. At column 12, lines 3-7, the patent states: "The product left after evaporation of excess $(CH_3)_2O$ and $CH_3Br$ was a viscous, pleasant-smelling liquid, which did not fume in contact with moisture as did the mixed methylbromosilanes." [Emphasis added] Since the products determine by GC and mass spec. analysis have recognized low viscosities, e.g., like water, the viscousness noted ("a viscous, pleasant-smelling liquid" in the above quoted paragraph) indicates that the methyl silsesquioxide (viz., $CH_3SiO_{1.5}$) that were present were too high boiling to show up in the analyses and were in the form of highly cyclized higher molecular weight resins. This further suggests that these relatively nonvolatile resins coated the reaction sites of silicon particles, interfered with fluidization, and inhibited further reaction. Though not reported in the patent, the experiment cited in Example 5(b), stated to have operated for 7 hours, resulted in a turnover of about 20% of the silicon metal in the initial fluidized bed. That suggests a silicon conversion of ~2.86% per hour, which accords with a typical direct reaction Si conversion rate, see Tables 4 and 5, at col. 21 of Lewis and Childress, U.S. Pat. No. 4,864,044. It is believed that a single bed turnover was not possible because too much resin blocked the Si reaction sites, thus shutting down the reaction.

Example 5(a) of the Lewis and Kanner patent is most interesting and relevant to understanding this invention. It states: "The reaction of Example 2 was repeated with 0.83 std. lit./min $CH_3Br$ over a 22 hour period. 591.34 gm of mixed methylbromosilanes was obtained after distillation of excess methyl bromide. The product contained 41.10 wt % $(CH_3)_2SiBr_2$, 33.06 wt % $CH_3SiBr_3$, 22.23 wt % $(CH_3)_3SiBr$, 0.57 wt % $(CH_3)_2SiHBr$, 0.22 wt % $CH_3SiHBr_2$ and 2.92 wt % methylbromodisilanes." The amounts of dimethyldibromosilane per trimethylbromosilane (D/M of 1.85) and dimethyldibromosilane per methyltribromosilane (D/T of 1.243) are exceptionally low. Compare that with the results of Example 2 where methyl chloride is used instead of methyl bromide. In the case of Example 2, 89.93 weight % $(CH_3)_2SiCl_2$, 4.58 weight % $CH_3SiCl_3$, 1.06 weight % $(CH_3)_3SiCl$, 1.11 weight % $CH_3SiHCl_2$ and a total of 3.32 weight % of a variety of methylchlorodisilanes and methylchlorosiloxanes, were obtained. In this case, the ratios of dimethyldichlorosilane to methyltrichlorosilane (D/T of 19.64) and trimethylchlorosilane (D/M of 84.84) are essentially normal to what one would expect from a commercial Rochow direct synthesis (see Equation I supra re: first stage of the Rochow direct synthesis).

Example 5(a) of Lewis and Kanner used the same bed and catalyst employed for making methylchlorosilanes to make methylbromosilanes and the catalyst/promoter of 5(a) was used for the reaction employing dimethyl ether as characterized in Example 5(b). No optimization of the catalyst system was undertaken to carry out the direct reaction using methyl bromide.

Yu. P. Endovin, et al. "Ethylchlorosilanes Manufacturing and Application of Product on their Base", page 253-264 of Silicon for the Chemical Industry IV, Geiranger, Norway, Jun. 3-5, 1998, Trondheim, Norway 1998, establish that the direct process has been commercially employed to make ethylchlorosilanes in a manner analogously employed to make methylchlorosilanes.

Direct Reaction to Make Trimethoxysilane from Methanol and Silicon

Trimethoxysilane is a recognized corrosive hazardous material.[13] It may decompose upon exposure to air or water and it is incompatible with strong oxidizing agents, strong bases and strong acids. It is very toxic and may be fatal on inhalation. Also, it may cause blindness. It is harmful if swallowed and in contact with skin. It is very destructive of mucous membranes. When methanol is reacted with silicon under direct reaction conditions, the reaction is highly exothermic, more so than the direct synthesis for forming methylchlorosilanes.

[13] http://physchem.ox.ac.uk/MSDS/TR/trimethoxysilane.html

In view of the environmental hazards of trimethoxysilane and the highly exothermic characteristics of the direct synthesis between methanol and silicon, one would expect that those skilled in the art would be reluctant to commercialize such a process in a fluidized bed reactor. However, the other methods for making trimethoxysilane were so economically unattractive that the art accepted the risks in order to develop methods for effecting the controllable reaction between methanol and silicon. In order to achieve this, the first order of business was devising a method for controlling the high heat generated by the reaction. The art turned to the use of inert liquids in which to slurry silicon metal and to control heat generation.

In an initial effort, Rochow, U.S. Pat. No. 3,641,077, patent in Feb. 8, 1972, react a lower alcohol with silicon while the silicon is suspended in silicone oil as a finely divided mixture with copper to make alkoxy silanes. The alcohol is introduced below the surface of the suspension, that is, it is bubbled or streamed through the suspension while the suspension is at a temperature sufficient to effect the reaction.

Hisashi Muraoka, et al., U.S. Pat. No. 3,775,457, patented Nov. 27, 1973, describe a method for making alkoxysilanes by reacting alkanols with silicon in the presence of copper such as cuprous chloride in a liquid inert medium, a "synthetic oil," such as those of the formulae—

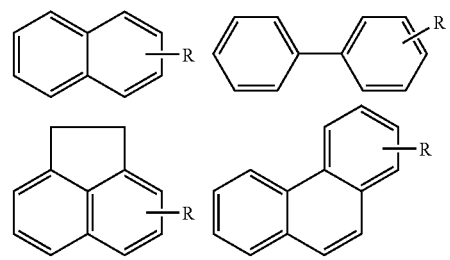

wherein R, in the foregoing, is an alkyl group having less than four carbon atoms. The use of oil in the Muraoka, et al. process "enables a catalyst and finely divided silicon to be uniformly dispersed in a reaction system, preventing the local generation of great heat in the reaction system and equalizing the temperature thereof." Simply put, the catalyst and the finely divided silicon are slurried in the oil. An advantage set forth in that patent is that the finely divided silicon can be activated in situ in the oil in the presence of inorganic and organic compounds of copper.

Ritscher, et al., U.S. Pat. No. 5,084,590, patented Jan. 28, 1992, describe a continuous process to produce trimethoxysilane by reacting methanol and silicon metal in the presence of a copper catalyst, viz.:

in a multi-reactor system. In this process, the activated silicon metal/copper catalyst are suspended in an inert solvent, essentially equivalent to that described in Mendicino, et al., U.S. Pat. No. 5,783,720, infra. Mendicino, et al., U.S. Pat. No. 5,783,720, patented Jul. 21, 1998, add a surface-active additive to this slurry phase direct synthesis of trialkoxysilanes. According to this patent, at column 1, lines 26-37, the slurry-process involves suspending catalytically-activated silicon particles in a thermally stable, high boiling solvent and reacting the silicon with an alcohol at an elevated temperature. Mendicino, et al. states that Rochow, U.S. Pat. No. 3,641,077, "teaches preparation of trialkoxysilanes by directly reacting copper-silicon mass, suspended in the silicone oil, with alcohol at 250°-300° C." Mendicino, et al. refer to Mendicino, U.S. Pat. No. 4,727,173, patented Feb. 23, 1988, which also describes a slurry process for making trialkoxysilanes by reaction of an alcohol with silicon metal in the presence of copper (II) hydroxide. At column 3 of Mendicino, lines 5-20, is the following description of solvents for dispersing the silicon metal and catalyst through which the alcohol is passed to effect the reaction:

The solvents useful in the process of this invention are inert solvents that do not degrade under the reaction conditions. The preferred solvents are high temperature stable organic solvents such as Therminol®59, 60 and Therminol®66, diphenyl ether and dodecylbenzene. THERMINOL® is the Monsanto Company trade name for heat transfer fluids. THERMINOL®60 is a polyaromatic compound with an average molecular weight of 250. Its optimum temperature range is from −45° to 315° C. THERMINOL® 66 is a modified terphenyl with an average molecular weight of 240. It has a higher upper temperature limit than the THERMINOL® 60: its maximum upper temperature limit is 371° C. The solvent is present in an amount sufficient to disperse the reactants homogeneously.

See as well, Medicino, et al., U.S. Pat. No. 5,783,720, Bailey, et al., U.S. Pat. No. 5,166,384, Moody, et al., U.S. Pat. No. 4,999,446, concerning this reaction system.

The effect of solvents in the direct reaction for trimethoxysilane from silicon and methanol is discussed by Lewis, et al., "Solvent Effects In The Direct Synthesis Of HSi(OCH$_3$)$_3$", page 307, Silicon for the Chemical Industry IV, Geiranger, Norway, Jun. 3-5, 1998, Norwegian University of Science and Technology, Trondheim, Norway. Standke, et al., U.S. Pat. No. 5,527,937, and Standke, "Direct Synthesis of Triethoxysilane, Chlorine Free Access to Organo-functional Silanes," page 225 Silicon for the Chemical Industry VI, Loen, Norway, Jun. 17-21, 2002, Norwegian University of Science and Technology, Trondheim, Norway, describe carrying out the direct reaction with an alcohol using tritoluenes, such as those of the formula:

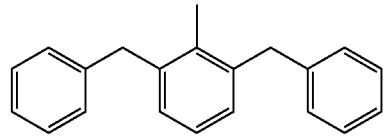

Brand, U.S. Pat. No. 6,380,414, is in many respects similar to the aforementioned Mendicino and Mendicino, et al. concerning the use of solvents. Brand describes making trialkoxysilanes by reacting silicon metal with an alcohol in an inert solvent in the presence of a copper catalyst, and contends that a halide free system is preferred. The copper catalyst contains a copper (II) oxide having a BET surface area of greater or equal to 10 square meters per gram. According to Brand, Okamoto et al., Lett. 33 (1995), 421 to 427, describe an investigation of the reaction of silicon metal with methanol in a silicon fixed-bed reactor over various copper catalysts. Brand states that the presence of chloride in the reaction mixture and in the product leads to a reduction in the yield of trialkoxysilane. Halide-free products are obtained by reacting silicon metal with alcohol in the presence of copper alkoxides. According to Brand, JP-A-05170773 describes the preparation of trialkoxysilanes by reacting silicon metal with alcohol in the presence of copper alkoxides. Halide-free products are obtained and the selectivity of the reaction is from 91 to 92% but the conversion of silicon is only from 21 to 32.4%. Brand states that JP-A-06065257 provides for an increase in the selectivity and in silicon conversion by using a copper alkoxide catalyst in combination with a metal halide. Brand asserts that the presence of a halide in the reaction mixture and in the reaction product has the disadvantages mentioned above. EP-A-0285133 is described by Brand as relating "to the preparation of trialkoxysilanes by reacting silicon metal with alcohols, a copper (II) hydroxide catalyst." Brand indicates that silicon conversions of from about 80 to 90 mol percent are achieved and the amount of tetraalkoxysilanes (i.e., tetraalkylsilicate) in the reaction mixture is from about 5 to 10 mol % based on the silicon. JP-A-10168084 is stated to describe the preparation of trialkoxysilanes by reacting silicon metal and alcohol over a copper (II) oxide catalyst which has a water content of less than 3000 ppm. Brand offers that "the low water content of the catalyst used may require a thermal pretreatment of the catalyst and hence an additional reaction step." According to Brand, the copper (II) oxide is "preferably freshly precipitated copper (II) oxide." Further preferences with respect to the catalyst are described by Brand.

The inert solvents described by Brand include heat transfer media such as heat transfer fluids that are sold under the Therminol, Dowtherm, Marlotherm trademarks, and such compounds as diphenyl ether, biphenyl, terphenyl and alkylated benzenes, alkylated biphenyls and alkylated terphenyl and reaction media which contain diphenylalkanes. Brand characterizes the solvents as having boiling points at atmospheric pressure which are higher than about 250° C. Brand carries out the reaction at from 150° to 300° C. The process described by Brand is carried out in a stirred reactor in which the copper catalyst is suspended in the liquid media.

According to Ritscher, "Managing A Technical Revolution: The Switch From Trichlorosilane To Trimethoxysilanes Based Processes," (page 265, Silicon for the Chemical Industry IV, Geiranger, Norway, Jun. 3-5, 1988, Norwegian University of Science and Technology, Trondheim, Norway) a commercial plant was started up in early 1997 in Termoli, Italy to make trimethoxysilane from the direct reaction of methanol with silicon metal. Mendicino, et al., "Trimethoxysilane Process Development From The Laboratory Scale Through Full Production," page 275, of the same journal, gives an overview of the chemistry and engineering start-up of the first commercial scale direct trimethoxysilane reactor.

Referring again to K. M. Lewis, et al., "Direct reactions of silicon with nanosized copper and copper compounds as catalyst precursors," Silicon for the Chemical Industry VI, pages 243-263, Loen, Norway, Jun. 17-21, 2002, Norwegian University of Science and Technology, Trondheim, Norway, the authors describe the general applicability of the use of solvent in carrying out the Rochow direct process, and surveys the prior art for early experiments showing the kinship between the conditions of running methyl chloride and alcohol within a copper catalyzed particulate silicon metal suspension to effect a Rochow direct process: the regimens cited in the article are incorporated herein by reference. According to this article and the prior art cited therein, the direct reaction to react methyl chloride with copper catalyzed silicon particles suspended in a solvent results in the efficient formation of dimethyldichlorosilane, much in the manner that it is formed by the fluidized bed process. Only a few reactions were needed to test that hypothesis.

Cyclic Dimethylsiloxanes

One of the most valuable precursors to making oils, elastomers and a wide variety of other silicones are the cyclic dimethylsiloxane monomers, i.e., the oligomers of the formula

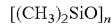

$[(CH_3)_2SiO]_n$ wherein $n$ is an integer of at least 3 and typically not greater than 7 though larger values are possible, but generally improbable, and invariably insignificant. The dimethylsiloxanes traditionally are formed by the hydrolysis and condensation of silanes having the formula

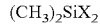

$(CH_3)_2SiX_2$ wherein X is a hydrolyzable group such as chlorine, bromine and alkoxide (such as methoxide and ethoxide). The hydrolysis and condensation can be effected under conditions which favor the formation of the cyclic dimethylsiloxanes of the above formula, see Noll, supra, pages 192-198. At page 192, Noll states:

Dimethyldichlorosilane gives with water a mixture of polymers containing either between 20 and 50% of polydimethylcyclosiloxanes or between 80 and 50% of linear polydimethylsiloxane-α,ω-diols, depending on the methods of working.

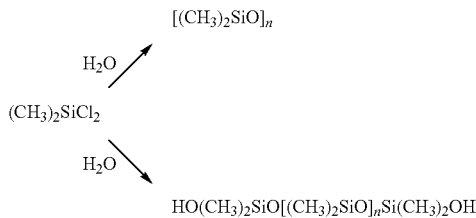

Hydrolysis with 6N aqueous hydrochloric acid instead of water, [sic] can increase the proportion of oligomeric cyclosiloxanes to about 70%.

Noll discusses at page 193 the use of organic solvents during hydrolysis of a halosilane. He indicated that toluene, xylene, diethyl ether, dibutyl ether, and trichloroethylene are frequently used as either immiscible or slightly immiscible solvents for including in the aqueous halosilane solution. At the bottom of the page, Noll states the following:

Because of the dilution of the siloxane phase, the tendency to intramolecular condensation predominates over intermolecular condensation and the difunctional siloxane units yield ring compounds preferentially. The lower polycyclosiloxanes are formed preferentially when dimethyldichlorosilane is hydrolyzed in ethereal solution.

At page 194, Noll states:

"Diethyldichlorosilane gives relatively good yields of low-molecular-weight cyclic polymers of the type [$D_3$] or [$D_4$] on hydrolysis in mixtures of alcohol and water." "The proportion of cyclics will depend on the substituents along the chain, the temperature and the presence of a solvent."[14]

[14] See: http://www.silicones-science.com/chemistry_cyclic.html

[Emphasis added]

Many years prior to the work leading to the invention of the Lewis and Kanner patent, laboratory studies examining some of the variables in the cyclic-linear equilibrium in the equilibration of dimethylsilicones (dimethylsiloxanes and polydimethylsiloxanes) confirmed Noll's report on the effects of solvents to favor the formation of cyclics. As conventionally known in the equilibration of cyclic dimethylsilicones employing either basic or acidic catalysis to form linear dimethylsilicone oils or dimethylsilicone gum stock, the studies established that when the process was completed the resulting product contained approximately 15% cyclics and 85% linears, by weight. When varying amounts of solvent were introduced to see the effect, if any, that solvents had on the amounts of cyclics and linears present at the end of the process, it was found as noted by Noll that as the amount of solvent was gradually increased there was dramatic shift in favor of cyclics at the expense of linears. When the amount of solvent present approached approximately 50 wt %, only cyclics were present at equilibrium. It was thus determined that on starting with a pure linear dimethylsilicone gum stock dissolved to the extent of 50 wt % in solvent, after equilibration the solution contained only cyclics. Similarly, on starting with cyclic siloxanes in a ~50 wt % solution, after equilibration only cyclics siloxanes, and no linear siloxanes, were present. In these equilibration experiments, cyclics were equilibrated with or without end-blocker with a determination of the amounts of cyclics and linears present at equilibrium. This work was repeated with the cyclics first dissolved in varying amounts of solvent, equilibrating the mixture and then re-determining the amounts of cyclics and linears present at equilibrium. A plotted graph of cyclics present after equilibration versus the amount of solvent present during equilibration established that above a certain minimum amount of solvent (somewhere between ~30 to ~60%), 100% cyclics were always present at equilibrium. This solvent effect orienting equilibration towards cyclic siloxane oligomers has been reported by Govedarica, "An alternative method for the determination of siloxane activities toward basic equilibration catalyst," J. Serb. Chem. Soc. 70 (12) 1461-1468, especially pp. 1465-6 (2005)[15] and Voronkov, V. P. Mileshkevich, Yu. A. Yuzhelevskii, The Siloxane Bond, Consultants Bureau, New York, 1978, pp. 160, 163.

[15] See: http://www.shd.org.yu/HtDocs/SHD/vol70/No12/JSCS_V70_No12-10.pdf

The boiling and melting points of the relevant cyclic siloxane oligomers (Rochow, *Chemistry of the Silicones*, Second Edition, 1951, page 83) are as follows:

| Name | Abbreviation | Boiling Point, °C. | Melting Point, °C. |
|---|---|---|---|
| Hexamethyltrisiloxane | $D_3$ | 134 | 64 |
| Octamethyltetrasiloxane | $D_4$ | 175 | 17.5 |
| Decamethylpentasiloxane | $D_5$ | 210 | −38 |
| Dodecamethylhexasiloxane | $D_6$ | 245 | −3 |
| Tetradecamethylheptasiloxane | $D_7$ | ~275-280* | — |

*obtained from other source

Synthesis Quality Silicon-Catalyst-Promoter

There is a large body of art directed to the quality (hereinafter referred to as "direct synthesis quality") of the silicon, catalysts and promoters useful in carrying out the direct synthesis/process. Commercial chemical and metallurgical grades of silicon metal for use in the Rochow direct reaction process that contain from 98 to 99.5 weight % silicon, ground to any specification, can be readily purchased with controlled amounts of various impurities such as Al, Fe, Cu, P, Zn, Sn, and the like, that have been shown to be beneficial in the direct synthesis of methylsilicon compounds. In addition, as illustrated herein, there is a large body of art directed to the general process parameters and protocols for carrying out the direct synthesis/process (hereinafter referred to as "direct synthesis parameters"). For good overviews, see Kanner and Lewis, "Commercial Production of Silanes by the Direct Synthesis" the Lewis Report, supra, and K. M. Lewis, et al., "Direct reactions of silicon with nanosized copper and copper compounds as catalyst precursors," supra. Lewis and Kanner, U.S. Pat. No. 4,593,114, at column 4, line 60 to column 5, line 2, characterize the pre-activated silicon as: "preferably technical grade material containing about 90-98% by weight Si, with the remainder composed of such elements as Fe, Ca, Mg, Al, Sn, B, Cu, Cr, Zn, Ti, Cd, Bi and Sb and other impurities. However, in the examples, they used a 98.4% pure silicon metal material. Impurities present in technical grade silicon have been described by Lobusevich, et. al. [(Russ. J. Appl. Chem. 49 (10), 2236 (1976)]. Preformed metal silicides such as those of iron, calcium, magnesium and copper may also be employed in the synthesis either as individual phases or admixed with elemental silicon." Rochow and Patnode, U.S. Pat. No. 2,380,996, patented Aug. 7, 1945, describe the next step of activating the silicon, and they describe the silicon component as a "solid, porous contact mass obtain by firing under reducing conditions porous bodies formed, as by molding, from a mixture of powdered silicon and powdered copper or other metallic a catalyst for the reaction." (See page 1, column 2, lines 19-21) The examples of the patent describe how the aforementioned "solid, porous contact mass" may be obtained. K. M. Lewis and T. E. Childress, U.S. Pat. No. 4,864,044, patented Sep. 5, 1989, offer an excellent review concerning direct synthesis parameters of silicon activation, copper catalyst manufacture and function and the role of the important promoters such as zinc and tin. The patent characterizes the distinction between catalyst/promoter made by the "cementation processes" which produce "cement catalysts" and are to be distinguished from "non-cement catalysts." (See column 3, lines 1, to column 5, to lines 18). However, Kanner and Lewis, "Commercial Production of Silanes by the Direct Synthesis", supra, at page 12, note that the use of cement copper catalysts has waned owing to its commercial unavailability and further teach that "non-cement copper catalysts are produced by atomization and partial oxidation of molten copper, by the partial oxidation of electrolytically or chemically produced copper, or by the incomplete reduction of cupric oxide." Lewis and Childress teach that the catalyst may contain 0.05-1.0 wt % zinc and about 0.001-0.1 wt % tin, based on the weight of silicon used. According to Lewis and Childress the amount of copper may be about 3 wt % or less.

Taken further, Ward, et al., U.S. Pat. No. 4,500,724, patented Feb. 19, 1985, in describing the prior art, notes that Gilliam, U.S. Pat. No. 2,464,033, "teaches that a proportion of from about 2 to about 50% by weight of copper in elemental form or as the halide or oxide, and preferably 5 to 20% and from about 0.03 to about 0.75% by weight of zinc in the form of zinc halide, zinc oxide, or zinc metal, or mixture thereof, where the weight of copper and zinc are based on the weight of silicon, can be used as a promoter for making dialkyl substituted dihalogenosilanes, such as dimethyldichlorosilane in the direct reaction between silicon powder and methyl chloride." Ward, et al., in referring to the work of Radosavlyevich, et al. (column 1, lines 44-53), noted "that micro quantities of silver added to contact masses resulting from the reaction of powdered silicon and methyl chloride in the presence of cuprous chloride decreased the yield of methylchlorosilanes, while tin and calcium chloride increased the rate of formation of methylchlorosilanes." Ward, et al. defined their contribution as carrying out the direct method "in the presence of and affective amount of a copper-zinc-tin catalyst" to enhance the selectivity of the reaction in producing dimethyldichlorosilane. This catalyst combination is described as superior in selectivity to that obtained with tin promoted copper catalyst and zinc promoted copper catalyst (see column 2, lines 49-69).

The Lewis Report emphasizes the importance of Ward, et al.'s promoter work as a benchmark "in Direct Process literature because without controlling the levels of Sn, Zn and other promoters other effects are equivocal." Ward, et al. established some direct synthesis parameters by devising a "catalyst system consisting of Cu, Zn, and Sn . . . which yielded 90% Di [i.e., Dimethyldichlorosilane] with nearly complete Si utilization. The trace elements in silicon used were (ppm): Fe (5600), Al (2700), Ti (850), Mn (200), Ca (160) and Ni (120) and the silicon was ball-milled to give particles with a surface area of 0.5 $m^2/g$. Pure CuCl was used and the zinc added also contained (ppm): Pb (1700) and Cd (170). Pure tin and methyl chloride were employed in the experiments. The best rate and Tri/Di [i.e., methyltrichlorosilane/dimethyldichlorosilane] were obtained when element ratios were: Cu (5%), Zn (0.5%) and Sn (0.005%). When tin was >2200 an increase in residue occurred. Further work was done . . . on the effect of tin and zinc" [See: W. J. Ward, G. L. Gaines, A. Ritzer, Brit. Pat. Appl. GB 2119808, CA 100:103630; W. J. Ward, G. L. Gaines, A. Ritzer, Offen. DE 3312775, CA 100: 68521.]. See as well, Diet-mar Seyferth, *Organometallics*, 20 (24), 4978-4992, 2001.[16]

[16] http://journals.iranscience.net:800/Default/pubs.acs.org/cgi-bin/jtextd@orgnd7_2F20_2F24_2Fhtml_2Fom0109051.html According to The Lewis Report, Kim and Rethwisch [J. P. Kim, D. G. Rethwisch, *J. Catal*, 134, 168 (1992)] in further investigating the affect of tin and zinc on the methylchlorosilanes direct reaction, ball milling was used to grind copper and silicon and to impregnate the mixture with tin and zinc. When MeCl (i.e., methyl chloride) "was passed over the balled milled mixtures silanes began to form at 147° C. with a maximum production at 317-347° C. When the catalyst consisted of only copper and zinc, MeCl decomposed without formation of silanes. However when MeCl reacted with copper and tin, some $Me_xSiCl_{4-x}$ was observed. Reacting MeCl with SiZnSn gave 64% $MeSiCl_3$. The addition of zinc to the MCS [i.e., methylchlorosilanes direct reaction] bed decreased the coking rate. Furthermore, surface chlorine was necessary for direct reaction; Zn and Sn promote its formation. Consistent with the synergism reported by Ward et al, zinc was found not to increase the overall rate but increased the selectivity for methylated silanes. Tin increased the selectivity for chlorinated silanes. Tin and zinc together increased the rate of the MCS reaction." In addition, The Lewis Report advises on the studies of the effects of tin, zinc and antimony on the catalyst system.

Kim, et al., "The effects of promoters on the Direct Process for methylchlorosilane", page 175, *Silicon for the Chemical Industry VI*, Loen, Norway, Jun. 17-21, 2002, Norwegian University of Science and Technology, Trondheim, Norway, discuss the selection of "optimum levels of zinc, tin and phosphorus" to yield 94 wt % dimethyldichlorosilane. The authors employed technical grade silicon with numerous trace elements having a surface area of 5 $m^2$ per gram. The copper source was copper (I) chloride and copper (II) oxide mixture having a surface area of 5.7 $m^2$ per gram and an average particle size of 30μ. They utilized a low Cu/Zn ratio enhanced by a small amount of phosphorus. Zinc levels of "approximately 0.1-0.2%" gave lower reaction rates but the T/D ratio "was at a minimum." Tin was shown to have a significant effect on rate of reaction. "At the value above 0.0004% the rate was approximately 3 times or more the one obtained with no tin." The authors note that phosphorus is a powerful dimethyldichlorosilane promoter and lowers the T/D but that the effect of phosphorus on the reaction rate was "small" and when the concentration was significantly increased there was a decrease in the reaction rate.

K. M. Lewis, et al., "Direct reactions of silicon with nano-sized copper and copper compounds as catalyst precursors," supra, show that too high a concentration of zinc promoter can adversely affect the D/T ratio in the slurry formation of dimethyldichlorosilane. A high D/T ratio was readily obtained by simple adjustment in the amount of promoter used in carrying out the reaction.

Standke, "Direct Synthesis of Triethoxysilane, Chlorine Free Access to Organofunctional Silanes," pages 225-231 of *Silicon for the Chemical Industry VI*, supra, describes the use of partially soluble copper salts of neocarboxylic acids in the direct reaction to make triethoxysilane.

Lewis and Kanner, U.S. Pat. No. 4,593,114, carefully address the activation of silicon metal as such relates to using methyl bromide or chloride and dimethyl ether reactants. They instruct that pure silicon does not react with methyl chloride below about 400° C., and even atomic silicon is non-reactive towards dimethyl ether. Consequently, silicon must be activated to achieve the combined reaction involving methyl bromide or chloride and dimethyl ether. Copper is the preferred activator "because it allows the lowest reaction temperatures to be used;" however, they note the suitability of silver for this purpose. Rochow (second edition), supra, at page 38, notes, "in general, the lowest temperature that will suffice to initiate the reaction has been found to be the most satisfactory for producing maximum yield of $R_2SiX_2$." According to Lewis and Kanner, at column 4, lines 13-18, the same reactor used for activation may also be used for subsequent reaction with methyl bromide or chloride and dimethyl ether. They point out that the silicon activation and reaction may be conducted in a separate reactor, provided the activated silicon is maintained in an inert atmosphere when transported to the reactor where the subsequent reaction is carried out. Essential to activation of silicon is that the activator such as copper be in intimate contact to permit diffusion of copper or other activator therein, thereby forming alloy or solid-solution with the silicon. Because copper is known to have a high diffusion rate in the silicon, increasing with temperature, temperatures above about 300° C. are "commonly employed for activation." Incorporated herein by reference, is column 4, lines 37-59 of the Lewis and Kanner patent. Activation of silicon may be effected by acid treatment (e.g., HCl and HF) or by hydrogen treatment.

There is a strong desire in the silicones industry from the early work of Rochow to the present to effect the direct reaction in such a manner as to avoid the undesirable costs and hazards currently inherent in the formation of methylchlorosilanes. More particularly, there is a strong desire in the silicones industry to avoid the significant cost contribution of silanes distillation to the costs of producing silicones. In addition, the silicones industry seeks a process for making silicones without the need of hydrolyzing methylchlorosilanes such as dimethyldichlorosilane which results in the formation of aqueous HCl. Further, the art seeks a process for producing dimethylsilicones which does not suffer from bed hot-spotting, bed gradation, vapor-borne fines generation (elutriation), bed agglomeration, and bed coking issues. The art seeks a method for making dimethylsiloxanes that avoids the problems associated with stages I-V cited above of the current Rochow process for making dimethylsiloxanes. Also desirable is a direct reaction that avoids the various problems associated with the formation and isolation of methylhalosilanes such as dimethyldichlorosilane, producing instead dimethylsiloxanes in a single step reaction, and doing so at a rate of silicon consumption that exceeds that formed by the direct reaction of methyl chloride with silicon.

The process of this invention materially contributes to meeting these strong desires by reducing the aforementioned cost and hazards, by avoiding the isolation of halosilanes, by materially reducing distillation requirements, by materially reducing the necessity of handling hazardous materials, and by eliminating steps in the prior art in making silicones and recovering chlorine values; thus, materially reducing processing costs and capital investment for the commercial manufacture of silicones by way of the direct synthesis.

THE INVENTION

This invention encompasses a solvent composition and a process for making it, wherein the solvent composition is essentially free of silicon bromide and comprises cyclic dimethylsiloxane oligomers dissolved in an inert liquid solvent containing insoluble direct synthesis quality silicon metal particles suspended in the inert liquid solvent, and a direct synthesis quality copper compound associated with the silicon metal particles. This composition is suitable for the recovery of the cyclic dimethylsiloxane oligomers from the suspended silicon particles and the copper compound, which can be used in conventional processes and compositions, and the use of the resulting suspension in a direct reaction to produce methylsilicon containing products such as this solvent composition.

In addition, this invention comprises a continuous silicon direct reaction process carried out within a direct process reaction zone to produce a product mixture that is predominantly cyclic dimethylsiloxane oligomers and recovering the cyclic dimethylsiloxane oligomers from the reactions zone.

This invention encompasses a process for making cyclic dimethylsiloxane oligomers by continuously feeding dimethyl ether and methyl bromide into an inert liquid suspension of direct synthesis quality particulate silicon metal associated with direct synthesis quality copper catalyst. The reaction is carried out under conditions that favor the formation of cyclic siloxane oligomers. As used herein, the term cyclic siloxanes oligomers represent any one of or the mixture of $D_{3-7+}$ siloxanes.

This invention relates to a cyclic and continuous process for making cyclic siloxane oligomers by continuously feeding dimethyl ether and methyl bromide into an inert liquid suspension of direct synthesis quality particulate activated silicon metal associated with direct synthesis quality copper catalyst with or without added promoter, but preferably with added promoter. The reaction is carried out under conditions that favor the formation of cyclic siloxane oligomers within the inert liquid suspension. Cyclic siloxane oligomers are recovered continuously from the reaction dissolved in the inert liquid suspension and separated from the inert liquid by distillation. Recovered inert liquid is recycled to the reaction.

This invention relates to a process for making cyclic siloxane oligomers by continuously feeding dimethyl ether and methyl bromide into a suspension in an inert liquid solvent of direct synthesis quality particulate silicon metal associated with direct synthesis quality copper catalyst, with or without added promoter, and effecting a reaction at a temperature of at least 200° C. under conditions that favor the formation of cyclic dimethyl siloxane oligomers within the inert liquid suspension.

This reaction is most effective when carried out with metallic copper or copper compounds as the activator and catalyst. Copper compounds and/or silicon compounds which contain other promoting or activating materials such as phosphorus, tin, zinc, aluminum, and the like, are particularly favorable.

In another and preferred embodiment, this invention comprises a continuous silicon direct reaction process carried out within a direct process reaction zone by reaction between methyl bromide, dimethyl ether and activated silicon particles to produce methylsiloxanes, the proportion of dimethylsiloxane produced in said reaction zone is greater than 75 mole % of the methylsiloxanes produced from said reaction and recovering the dimethylsiloxane from the reaction zone.

This preferred embodiment of the invention relates to a novel continuous process for making dimethylsiloxane directly by the reaction at an elevated temperature of a mixture of methyl bromide and dimethyl ether within a dynamic bed of thermally activated silicon metal particles associated with copper catalyst and promoter, while the bed is agitated by either gas fluidization or by stirring, especially while in the form of a slurry in an inert liquid solvent, such that there is at least one complete silicon metal bed turnover during the continuous process and the proportion of dimethylsiloxane produced in said bed is greater than 75 mole %, preferably greater than 80 mole %, of the methylsiloxanes produced from said reaction.

In a further aspect of this preferred embodiment of the invention, the major portion of the dimethylsiloxane produced in the bed is cyclic dimethylsiloxane oligomers. In a further preference of this embodiment, when using an agitated inert solvent slurried bed, essentially all of the dimethylsiloxane is cyclic dimethylsiloxane oligomers.

In a preferred practice of this invention, methyl bromide formed in the reaction is recycled back to the reactor as part of a recycle stream. In such practice, methylsiloxanes are the only products of the reaction and they are recovered by separation from the bed whether fluidized or in a inert solvent slurry.

This invention encompasses a solvent composition and a process for making it as afore-defined, wherein the proportion of dimethylsiloxane in said composition is greater than 75 mole %, preferably greater than 80 mole %, of the methylsiloxanes present therein. This composition is suitable for the recovery of the cyclic dimethylsiloxane oligomers from the suspended silicon particles and the copper compound, which can be used as such and in conventional processes and compositions, and as well, the use of the resulting suspension in a direct reaction to produce methylsilicon containing products such as this solvent composition.

In addition, this invention comprises a continuous silicon direct reaction process carried out within a direct process reaction zone to produce a product mixture that is predominantly cyclic dimethylsiloxane oligomers, the proportion of dimethylsiloxane produced in said reaction zone is greater than 75 mole %, preferably greater than 80 mole %, of the methylsiloxanes produced from said reaction and recovering the cyclic dimethylsiloxane oligomers from the reactions zone.

This invention encompasses a process for making cyclic dimethylsiloxane oligomers by continuously feeding dimethyl ether and methyl bromide into an inert liquid suspension of direct synthesis quality particulate silicon metal associated with direct synthesis quality copper catalyst and direct synthesis quality promoters. The reaction is carried out under conditions that favor the formation of cyclic siloxane oligomers. As used herein, the term cyclic siloxanes oligomers represent any one or more of the mixture of $D_{3-7+}$ siloxanes.

This invention relates to a cyclic and continuous process for making cyclic siloxane oligomers by continuously feeding dimethyl ether and methyl bromide into a fluidized bed or an inert liquid suspension of direct synthesis quality particulate activated silicon metal associated with direct synthesis quality copper catalyst with added promoter. The reaction is carried out under conditions that favor the formation of cyclic siloxane oligomers within the fluidized bed or inert liquid suspension. Methyl bromide formed in the reaction is recycled back to the feed stream and used in maintaining the continuous process. Cyclic siloxane oligomers are recovered continuously from the reaction either neat (i.e., free of solvent other than products from the reaction) or dissolved in the inert liquid suspension depending on whether the bed is fluidized or in the form of a solvent suspension and recovered from other materials (e.g., other methylsiloxanes components in the reaction product) by distillation or separated from the inert liquid by distillation. Recovered inert liquid is recycled to the reaction.

This invention relates to a process for making cyclic siloxane oligomers by continuously feeding dimethyl ether and methyl bromide into a fluidized bed or suspension in an inert liquid solvent of direct synthesis quality particulate silicon metal associated with direct synthesis quality copper catalyst, with or without added promoter, and effecting a reaction at a temperature of at least 200° C. under conditions that favor the formation of cyclic dimethyl siloxane oligomers and the proportion of dimethylsiloxane produced in said bed or suspension is greater than 75 mole %, preferably greater than 80 mole %, of the methylsiloxanes produced from said reaction within the fluidized bed or inert liquid suspension.

This reaction is most effective when carried out with metallic copper, soluble or insoluble copper compounds as the activator and catalyst in combination with zinc and tin promoters. Copper compounds and/or silicon compounds which contain other promoting or activating materials such as phosphorus, tin, zinc, aluminum, and the like, are particularly favorable. The reaction is most effective when there is used zinc and tin promoters and their content in the reaction are each from about 0.005 to about 1 weight % of the silicon metal in the bed and most preferably, they are used in essentially the same weight %.

DETAILED DESCRIPTION OF THE INVENTION

Figure 1:
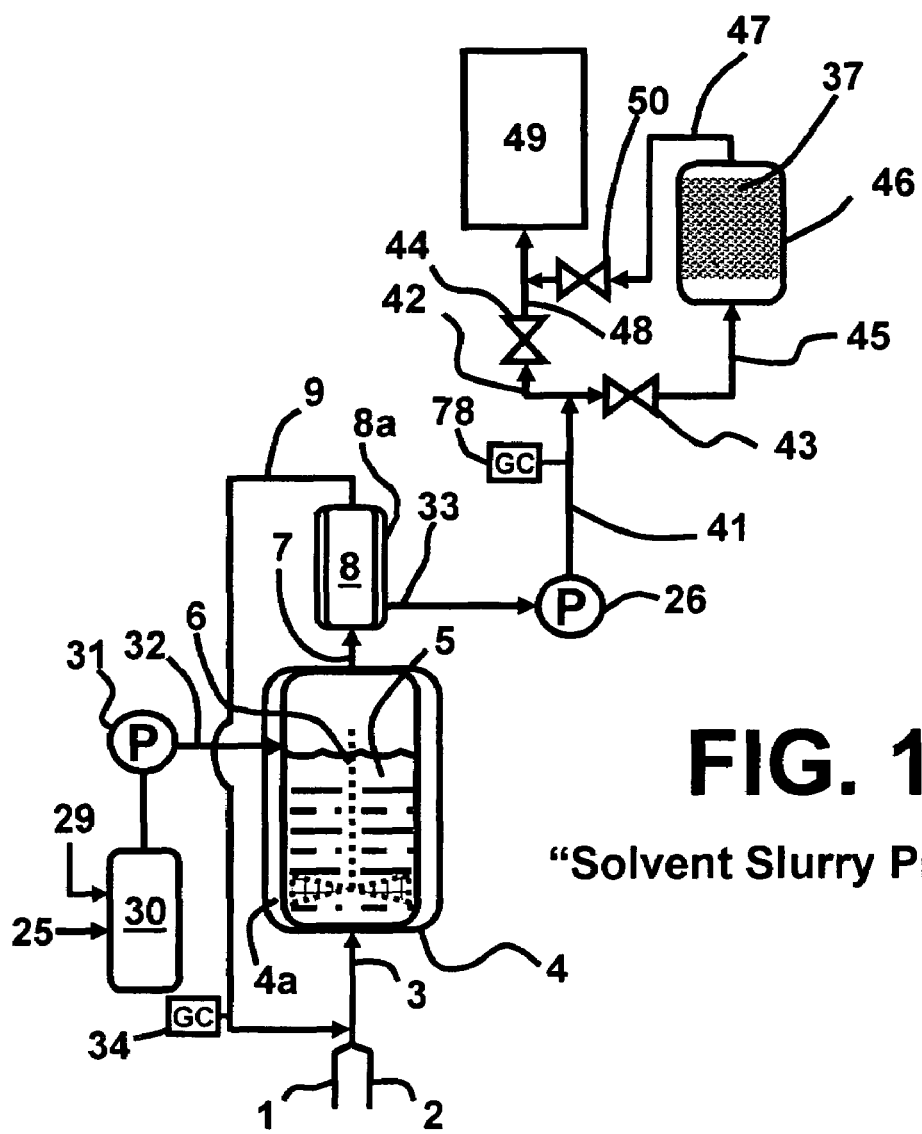
FIG. 1 depicts schematically a plan view of apparatus and material flow for practicing the inert solvent slurry process of this invention to produce the dimethylsiloxane compositions of this invention. In this embodiment, FIG. 1 relates to the use of conventional equipment employed in the chemical industry to provide the advantages herein described.

The silicones industry has wedded itself for about 60+ years to making linear and cyclic dimethylsiloxanes by the hydrolysis of dimethyldichlorosilane, which necessitates making dimethyldichlorosilane by the Rochow direct process, even though there was an industry desire to avoid the undesirable costs and hazards inherent in that approach. More than twenty years since the discovery of Lewis and Kanner, the industry has failed to appreciate that there are elements of technology in the silicones field which can be combined to meet the strong desire of avoiding the significant cost contribution of chlorosilanes distillation and hydrolysis in making these silicones and render commercially possible the effective continuous reaction between methyl bromide and dimethyl ether to form an essentially bromine-free silicone product that is widely recognized to be preferred precursors in the manufacture of silicone fluids, oils, rubber, and a host of other silicone based materials.

The Lewis and Kanner patent demonstrates in Example 5(b) that dimethyl ether and methyl bromide can react in a fluidized bed to produce methylsiloxanes directly. The deficiency in that example is the fact that the catalyst/promoter used in Example 5 is the same catalyst/promoter employed for making dimethyldichlorosilane and Example 5(a) demonstrates the poor product distribution obtained when methyl bromide is used instead of methyl chloride. There is hereinafter described a catalyst/promoter system that achieves high D/T selectivity for the reaction of methyl bromide with silicon, which high D/T selectivity is similar to that commercially obtained in making dimethyldichlorosilane, thereby solving the riddle of poor product distribution as obtained in Example 5(b) that yielded mixed methylsilicones predicated on the poor methylbromosilanes distribution of Example 5(a), viz.,

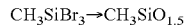

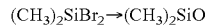

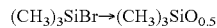

and the copolymers thereof. Such a catalyst/promoter system results in high dimethyldibromosilane selectivity in the range of 85% or greater, assuring a dimethylsiloxane productivity of at least 75 mole %, preferably at least 80 mole %, and most preferably at least 90 mole % of the methylsiloxanes produced. In the most preferred embodiment of the invention, the dimethylsiloxane productivity ranges in a continuous operation over 85-90 mole per cent of the methylsiloxanes produced. Operation of the process in a solvent silicon metal slurry has the significant advantage of favoring up to 100 mole per cent conversion of the produced methyl siloxanes to cyclic dimethylsiloxane oligomers, however, in the typical case, some minor amount of methylsiloxanes resin, linear dimethylsiloxane and some minor amount of end-capped fluid dimethylsiloxane are to be anticipated.

One of the characteristics that measures the effective performance of a Rochow Process fluidized bed operation in making of dimethyldichlorosilane, is the rate of silicon metal consumption per hour, measured in pounds/hour or percent of the bed per hour, and the cycle of beds turned over before the reactor is shut down. If the silicon metal consumption (or % of silicon relative to bed size that is added to the bed per hour) is 5%, then a bed turnover is rated as 20 hours, and thus each 20 hour cycle is consider to be a single bed turnover. In the Rochow Process, the rate per hour is typically below about 3.5%. In the usual practice of this invention, the silicon metal consumption per hour is at a rate of at least 3.5% and may be as high as 10%; however, the usual hourly Si consumption rate may be in the range of 4-8%.

K. M. Lewis demonstrated the simplicity of making high yields of dimethyldichlorosilane in a slurried direct reaction. However, he did not extend this to the process of reacting methyl chloride or bromide and dimethyl ether with silicon in a solvent slurry. The individual principles of this invention, such as selection of silicon metal, its activation, its catalysis, its promotion and its reactivity with methyl bromide and dimethyl ether, are fully embodied in the prior art and are well within the capabilities of the skilled worker in the art. This invention provides the heretofore unanticipated linkage of these principles to achieve a process that is not reliant on chlorosilane isolation and subsequent chlorosilane hydrolysis. Long ago, as noted by Noll, supra, page 193 the presence of solvents in the condensation of dimethyldihalosilane hydrolyzate and the equilibration or intramolecular condensation of linear and cyclic dimethylsiloxanes results in the formation of predominantly if not total conversion to $[(CH_3)_2SiO]_n$ product. Indeed, the use of solvents in making trimethoxysilane by the silicon direct reaction, a very exothermic reaction, is well appreciated, but not for the purpose of an in situ conversion of the reaction product of the catalyzed reaction between methyl bromide, dimethyl ether and silicon to form dimethylsiloxanes, and in particular, cyclic dimethylsiloxane, i.e., $[(CH_3)_2SiO]_n$.

It is believed that the process of the invention comprises inter alia the in situ reactions characterized in the following sets of equations embraced within the circumscribing brackets.

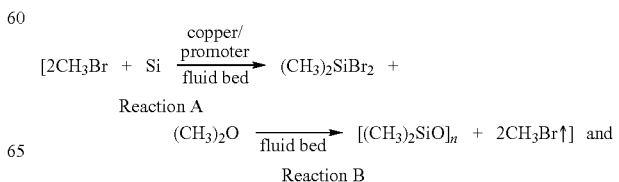

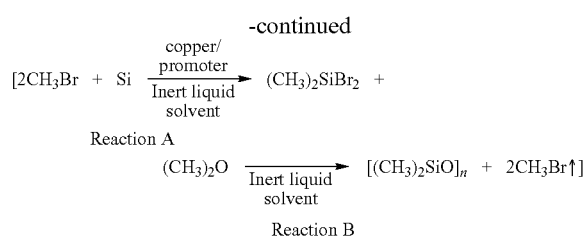

In the foregoing, Reaction A occurs simultaneously and concurrently with Reaction B. In the above equation, "n" is an integer of at least 3 and typically not greater than 7, but may have a very small concentration of $[(CH_3)_2SiO]_n^1$ where "$n^1$" has a value greater than 7. Consequently, Reactions A and B operate in a fluid bed or in an inert liquid solvent slurry within which is suspended the silicon metal and within which is provided the copper catalyst/activator and the promoter. From the above, it is apparent that Reaction A will be controlling with respect to the results of Reaction B. If Reaction A achieves solely dimethyldibromosilane, then Reaction B will comprise the classic reaction expected resulting in essentially cyclic dimethylsiloxane oligomer, and it follows that the proportion of dimethyldibromosilane derived from Reaction A will essentially reflect the proportion of cyclic dimethylsiloxane oligomer present in the methylsiloxanes derived from Reaction B. Both reactions, because of their in situ nature, operate at the same temperature and pressure. By consolidating the reactions, the in situ effect is as follows:

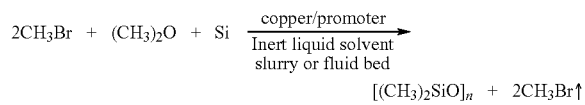

Unreacted dimethyl ether is withdrawn from the reaction with off-gas methyl bromide. An advantage of this process is evident from these equations, which show methyl bromide to be a gaseous product removed from the desired methylsiloxanes product(s). In the case of the Rochow Process, the product of the reaction ties up the Cl in the desired product of the reaction and that has to be removed and recovered by multiple steps which consequently causes Cl loss to neutralization and landfill before it can be recovered and recycled as methyl chloride to the reaction. Such does not occur in the process of this invention, which allows the methyl bromide formed in the reaction zone to be easily recovered separate from the methylsiloxanes product of the reaction, and directly recycled to the reaction to produce more methylsiloxanes product. This facet of the process reduces recovery costs of the bromide which mitigates any differential in the purchase cost of methyl bromide versus methyl chloride because less purchased methyl bromide is required for makeup purposes. Because methyl bromide in the cycle is essential constant, the initial feed of methyl bromide only requires a small makeup amount of methyl bromide to be fed to the reaction cycle once the reaction cycle is well established.

The desired product of the reaction $[(CH_3)_2SiO]_n$ (or including the dimethylsiloxanes, and other methyl silicones made in a fluid bed operation) is isolated from the reaction by removal from the reaction zone in combination with the inert liquid solvent when employed, and residual silicon metal, copper catalyst/activator and promoter, from which it is isolated by distillation for recovery and further treatment, as required, for making other silicone products (as typically practiced in the art). This allows for recycle of the inert liquid solvent when employed (as in the slurry process), residual silicon metal, copper catalyst/activator and promoter to the reaction zone, as the case may be and as required. All of this may be done continuously, periodically or batchwise. Preferably, the process is operated continuously. Essentially no bromine containing silane is present, though very minor amounts of methoxysilane may be present, in the $[(CH_3)_2SiO]_n$ (or dimethylsiloxane in the case of the fluid bed process) product isolated from the reaction. In the course of reaction, it is to be expected that trifunctional silanes will react with dimethyl ether to form cyclic high boiling methyl siloxane resins, e.g., $[CH_3SiO_{3/2}]_x$, dissolved in the inert liquid solvent from the slurry reaction system or in the bed in the case when the reaction is carried out in a fluid bed. The economic feasibility of operating a fluid bed process will be dependent on the D/T ratio, which will determine the amount of silicone resin accumulated in the bed and the life of the bed. Because of its great difference in boiling characteristics, the desired $[(CH_3)_2SiO]_n$ product that is isolated by conventional distillation will be free of such resins. In addition, because of its relatively low boiling point, compared to that of the inert liquid solvent, the desired $[(CH_3)_2SiO]_n$ product is facilely isolated by simple distillation. The resin is typically not isolated from the inert liquid solvent or the fluid bed until its concentration in the solvent/bed adversely affects the performance of the process, a condition which is determined by process economics, handling issues, environmental issues, and the like. In the situation where the reaction between methyl bromide, dimethyl ether and silicon is performed inefficiently, as in the case with Example 5(b) of the Lewis and Kanner patent, the benefit of operating the process in an inert liquid solvent has the advantage of solvating the resin that is produced and keeping the silicon reaction sites available to continue the reaction up to at least a single bed turnover and materially increase the concentration of cyclic dimethylsiloxane oligomers in the resulting reaction product.

When resin buildup adversely affects the attractiveness of continuing operation of the process, resin separation may be performed as follows:

i. in the case of separation from a fluid bed, the bed is removed from the reactor and treated with a relatively low boiling solvent, such as toluene or xylene, and the resulting resin solution is distilled to recover the solvent and the cleaned up bed composition may be re-used in the fluid bed operation and the recovered solvent may be re-used for another bed treatment;

ii. in the case of separation from an inert liquid solvent slurry process, the slurry is filtered to remove the silicon particles, associated catalyst and promoter, and separated inert liquid solvent with dissolved resin is distilled to isolate a resin residue; inert liquid solvent recovered in the solvent cleanup step is reused by recycling it to the reaction.

Isolated resin may be treated with HF to bread down the resin for recovering of silicon. In the slurry process, cleanup step may be taken before or after the isolation of $[(CH_3)_2SiO]_n$ product from the inert liquid solvent. If product of the reaction is high in linear dimethylsiloxane oligomers in addition to the cyclic dimethylsiloxane oligomers, then the mixture may be treated to equilibrate the mixture to the cyclic oligomers.

In both the fluid bed process and the slurry process, it may prove to be more desirable to keep product in the entrained liquid silicones or the inert liquid solvent during the filtration step because of its low viscosity and its ability to reduce the viscosity of the bed or the inert liquid solvent and any resin therein. Thus, the product of the process can be a processing aid in the filtration step. It is to be understood that the term filtering and filtration step as used herein constitutes any viable method by which solid or condensed products are separable from a liquid body in which such products are not fully solvated, and includes procedures such as centrifugation (e.g., cyclone separation), filtration, decantation, combinations of them, and the like.

The process of this invention utilizes in a single step, in a single reaction zone comprising an inert liquid solvent, the reaction of methyl bromide with activated silicon metal suspended and slurried in sufficient high boiling inert liquid in the presence of a copper catalyst and Zn/Sn promoters and the in situ reaction of dimethyl ether concurrently provided in said reaction zone whereby to form dimethylsiloxane oligomers, especially cyclic dimethylsiloxane oligomers dissolved in the high boiling inert liquid in a concentration greater, on a percent by weight basis, than any other dimethylsiloxane component present in said inert liquid, preferably to the essential exclusion of any other dimethylsiloxane component.

Consequently there may be formed a composition comprising a solvent containing composition comprising cyclic dimethylsiloxane oligomers, that is, $D_{3-7+}$, in an inert liquid solvent containing suspended (e.g., slurried) silicon metal particles and a copper compound associated with the silicon; and a process for making the composition by continuously feeding dimethyl ether and methyl bromide into a suspension of direct synthesis quality particulate silicon metal suspended in an inert liquid solvent and associated with direct synthesis quality copper catalyst, within a reaction zone at a temperature of at least 200° C. and, preferably, under conditions that favor the formation of cyclic dimethylsiloxane oligomers dissolved in the solvent suspension. The process is preferably continuous by providing for the isolation of the cyclic dimethylsiloxane oligomers made in the reaction zone and the recycling to the reaction zone recovered solvent, silicon metal and catalyst, as well as recovered dimethyl ether and dimethyl bromide.

The components provided in the reaction zone are:

(1) Inert Liquid Solvent—The inert liquid solvent is a liquid that (a) has a boiling point greater than the highest boiling dimethylsiloxane product of the process of this invention, e.g., cyclic dimethylsiloxane product of the process of this invention, and (b) is thermally stable at that temperature. It typically represents a sufficient concentration of the liquids present in the reaction zone whereby it produces under the preferred conditions of this direct reaction, a concentration of principally $D_{3-7}$ by weight that exceeds the concentration of any other dimethylsiloxane component generated by the reaction that is dissolved in the inert liquid. Preferably, the inert liquid solvent represents at least about 30 wt % of the liquid content within the reaction zone, more preferably at least about 40 wt %, and most preferably at least about 50 wt %. On start up, inert liquid solvent would typically represent 100 wt % of the liquid within the reaction zone exclusive of liquid promoters and/or activators. A particularly desirable inert liquid is one which solvates all of the dimethylsiloxane oligomer, in particular, all of the cyclic dimethylsiloxane oligomers (i.e., $D_{3-7}$), and has a sufficiently high enough boiling point to allow straightforward separation of the oligomers by conventional distillation. Suitable inert liquid solvents include those which are chemically inert under the reaction conditions, have boiling points which are greater than the boiling point of $D_7$, more desirably greater than 300° C., preferably 330° C. or higher, and are thermally stable at these temperatures. The most preferred inert liquid solvents are those which have a boiling point in the range of about 50° C. higher than the boiling point of the highest boiling dimethylsiloxane oligomer present in the reaction mixture, especially the cyclic dimethylsiloxane oligomers formed in the course of the process. Such higher boiling point aids in the separation of the dimethylsiloxane products, e.g., cyclic dimethylsiloxane oligomers, by distillation. The chemical nature of the inert liquid solvents should be such that they do not react in the course of the reaction between methyl bromide, dimethyl ether, and silicon metal nor do they react with any siloxane generated in the process: and they may be polar or nonpolar. By way of illustration of such inert liquid solvents are nonpolar hydrocarbons, such as: dodecylbenzene, butyl or higher alkylated biphenyls; SASOL 1050, SASOL 154L, SASOL 159L, SASOL 3050, SASOL 3060L-B, SASOL 7050, SASOL 8560L-H, and SASOL 9350L-O Specialty Alkylates from Sasol North America Inc.; Therminol® 66, Therminol® HT or Therminol® 72 heat transfer fluid, which has an operating range of from −10° C. to 380° C. (15° F. to 720° F.) [http://www.therminol.com/pages/products/72.asp], all obtainable from Solutia Inc.; Xceltherm® MK 1, LV 1, HT, XT, and HTR obtainable from Radco Industries; MCS 2811 and MCS 2809 from Solutia; Diphyl®, Diphyl® KT, Diphyl® THT, Diphyl® DT from LANXESS (Bayer A G, Leverkusen); and polar compounds illustrated by dodecylbenzonitrile, cyanobiphenyl ether, phenylbenzonitrile, tolylphenylsulfone and mixed isomers of ditolylsulfones. The amount of the inert liquid solvent is not narrowly critical, but should be sufficient to favor cyclic oligomer formation within the reaction zone. However, one can initially select the solvent concentration based on the amount of the silicon metal utilized in the process. That concentration can range from one part by weight of solvent for two parts by weight of silicon metal up to four parts by weight of solvent for each part of silicon metal. Generally, the solvent concentration will be equivalent, in terms of weight, to the amount of silicon metal, or will exceed that concentration.

(2) Direct synthesis quality activated particulate silicon metal particles. A significant advantage of the process of this invention relates to the non-criticality of the character of the silicon metal particles utilized in the process. As noted above, absolutely pure silicon metal is not reactive with metal halides; ergo, to be reactive, the silicon metal must have impurities in ppm concentrations such as Fe, Ti, Mn, Al, Ca and Ni, and the like. This invention employs the same kind of a relatively pure silicon metal that is used in the Rochow direct synthesis fluidize bed process. Typically, the silicon metal though containing impurities should have silicon purity of at least about 90 to 99.5+ wt %. The optimum level of purity fluctuates according to process variabilities, such as the nature of the catalyst and promoters that are employed, the reaction temperature, the method of activation, and the like issues. To appreciate this issue of non-criticality, one needs to contrast the characteristics of the process of this invention which relies upon the use of an inert liquid solvent and the process of the prior art which relies upon the use of a fluidized bed reaction system. In the prior art fluid bed direct synthesis systems, particle size for the purposes of fluidization is a very critical factor. That does not exist with the solvent slurry phase process of this invention. It remains a critical factor when carrying out the invention in a fluidized bed. According to K. M. Lewis, et al., "Direct reactions of silicon with nano-sized copper and copper compounds as catalyst precursors," supra, at page 243, "in slurry-phase Direct Reactions, elutriation does not occur" and, at page 244, "elutriation does not occur from slurry phase reactors." Thermal stability of the prior art fluid bed is a constant problem in the utilization of methyl bromide (including a co-reactant such as dimethyl ether), silicon, catalyst, promoter, and, silicon metal particles noted previously, because of the need for replenishment of the fluid bed because of coking, agglomeration, hot spots, and the like issues. That is not an issue with the solvent slurry process of this invention. It remains an issue in the practice of this invention when carried out in a fluidized bed. In addition, though it is recognized that a smaller particle size of silicon and the associated copper catalyst is desirable in the direct reaction process, too small a particle size fluidized bed process results in excessive formation of silicon metal fines that are blown from the bed: thus, imposing a restriction on maximization of the available silicon reaction surface area. Such inhibits the rate of reaction that one can reasonably attain in the fluidized bed direct reaction of the prior art. This feature is not a restriction in the practice of the solvent slurry process of this invention. Because the silicon metal is suspended in a liquid, a number of advantages occur: (a) heat of reaction is transferred from the silicon particles to the inert liquid solvent in such a manner as to avoid the occurrence of hot spots, particle agglomeration, coking, and the like; (b) silicon metal fines are maintained in the reaction zone with the inert liquid solvent, and are better sites for reaction because they increase the silicon metal, catalyst and promoter surface areas within the reaction zone, which increases the potential for higher rates of reaction while maintaining high D/T levels; (c) silicon metal particulates regardless of particle size are maintained in suspension during recycling of the inert liquid solvent, (d) the inert liquid solvent solvates byproduct cyclic methylsiloxane resin that may be formed in the reaction zone, which in a fluidized bed system coats the silicon particles and reduces available silicon metal surface area for reaction with methyl bromide, to the point of effectively shutting down the reaction; this solvating feature keeps the silicon particles free of the resin, which means there is less need for removing silicon metal from the recycle stream for cleanup and/or replenishment purposes; and (d) with the ability to enhance reaction rates, as noted above, it is possible to reduce the reaction temperature, which enhances reaction efficiency towards the production of desired cyclic dimethylsiloxane oligomers within the reaction zone. It is also possible to increase the reaction rate by progressively increasing the surface areas of the particulate silicon, catalyst and promoter, and thus the productivity of the process, and allowing one to increase the reaction temperature, at the same time avoiding hot spots, particle agglomeration, coking, and the like, because of the much higher heat capacity of liquid solvents as compared to gases.

The silicon metal source for the direct reaction is in particulate form and may embody a variety of compositions, such as that described by Rochow and Patnode, U.S. Pat. No. 2,380,996, supra, and it is notable that such silicon contains trace elements in ppm concentrations such as Fe, Ti, Mn, Ca and Ni, and the like. Lewis and Kanner, supra, employed preferred technical grade silicon containing about 90-98.5% by weight Si, with the remainder composed of such elements as Fe, Ca, Mg, Al, Sn, B, Cu, Cr, Zn, Ti, Cd, Bi and Sb and other impurities, noting that impurities present in technical grade silicon have been described by Lobusevich, et. al. [(Russ. J. Appl. Chem. 49 (10), 2236 (1976)]. Lewis and Childress, U.S. Pat. No. 4,864,044, column 10, lines 39-56, the teachings which are incorporated herein by reference, sets forth a preferred technical grade silicon as containing about 90-99%+ (preferably at a minimum of 98.5%) by weight silicon, with the remainder composed of the elements Fe, Ca, Mg, Al, Sn, B, Cu, Cr, Zn, Ti, Cd, Bi and Sb and other impurities, as noted in the prior art. According to Kanner and Lewis, "Commercial Production of Silanes by the Direct Synthesis", supra, at page 8 states, "the silicon employed in the Direct Synthesis . . . is commonly a technical grade material containing about 98-99 wt % Si." The quality (i.e., 98-99.5+%) of silicon metal is preferred for the practice of this invention. Most preferred, is the technical or chemical grade material containing about 98-99 wt % silicon. Preformed metal silicides such as those of iron, calcium, magnesium and copper may also be employed in the synthesis either as individual phases or admixed with elemental silicon. It has been frequently stated in the direct process art that the silicon metal can be any commercially available grade of silicon in particulate form. Because the slurry phase process of this invention does not rely on gas phase fluidization, there is no criticality of particle size of the solid silicon as would be an issue for effective fluidization. A typical composition of commercial silicon metal useful in this invention, expressed in percent by weight, is ~99% silicon; ~<0.50% iron; ~0.20 to 0.35% aluminum; ~<10 ppm lead; ~<20 ppm boron. Generally smaller particle size (~<500 microns) is preferred for ease of processing. Most preferably the particle size ranges from about 0.01 to 400 microns. Sieving of ground silicon to regulate particle size is optional. However, when the process of the invention relates to the fluidized bed process, then the limitations of the art in respect to silicon particle size and particle size distribution for such reaction systems are likewise limitations of this invention. A useful particle size distribution for the fluidized bed process is described by Freeburne, et al., U.S. Pat. No. 5,312,948, patented May 17, 1994.

As noted above, using smaller particle size silicon is advantageous for the reasons stated. However, inherent in the continuous operation of this invention which involves recycling of silicon particles to the reaction zone after removal of dimethylsiloxane reaction product, is the constant reduction of the average particle size of the silicon owing to depletion of surface silicon during the reaction. Concomitantly, the size and shape of the solid catalyst and promoters will be changed, e.g., they will become smaller and more rounded by normal solvent or gas attrition, also providing increased surface area which enhances their performance in the slurry process of the invention. Automatically, this reduction in particle size with concomitant makeup of silicon causes an increase in available silicon surface area for a given weight of silicon resulting in an increase in the reaction rate resulting in an inherent increase in the productivity of the process. Makeup silicon to the reaction zone provides the desired silicon concentration during the reaction. In the case of the fluidized bed process of this invention, this reduction in particle size can result in elutriation of the particle fines, and that is desirable to avoid. However, since the methyl bromide released from the reaction is recycled to the reaction, silicon and catalyst/promoter fines blown out of the bed and entrapped in the methyl bromide and excess dimethyl ether will also be recycled to the bed unless the fines are filtered from the methyl bromide (with or without dimethyl ether) stream. In this fashion, some portion of the fines may be repeatedly subjected to the reaction conditions and eventually consumed. However, because elutriation does not occur in the slurry phase process of this invention, this attribute of the process is quite beneficial. It is a mechanism for achieving high rate of production while not requiring overly ground silicon particles. It is possible to use this inherent increase in silicon surface area in the reaction zone as a mechanism for achieving maximized reaction rates and productivity while minimizing the cost of grinding the silicon particles as well any adverse effects from grinding such as surface oxidation of silicon. Of course, one might wish to finely grind the silicon-catalyst/promoter to extremely small size at the outset and recycle such in the course of the process, until its natural consumption.

(3) Catalyst The catalyst serves two functions: it activates the silicon so that it reacts with the metal bromide, thus it is often termed an activator, and it affects, in conjunction with the promoter, the rate of the reaction and the efficiency of the reaction to the desired D/T ratio. Such impacts on the efficiency to the desired dimethylsiloxane, e.g., the cyclic dimethylsiloxane oligomers. The preferred activator is copper because it allows the lowest reaction temperatures to be used. Silver is also suitable. The activator (e.g., copper) and silicon should be in intimate contact to permit diffusion of copper or other activator into the silicon and the formation of an alloy or solid-solution. Copper has a high diffusion rate in silicon and this rate increases with temperature [Ward and Carroll, J. Electrochem. Soc. Solid State Sci. Tech. 129(1), 227 (1982)]. The preferred catalyst is powdered metallic copper, but any anhydrous copper compound, and mixtures thereof, is within the contemplation of this invention. Illustrative anhydrous copper compounds, useful alone or in admixture, are the copper oxides. Temperatures above about 300° C. to about 400° C. are commonly employed for activation of the silicon. In the case of the preferred activator, i.e., copper, activation may be accomplished by, for example, solidifying a melt containing copper and silicon and comminuting the solid into particles; or by heating particles of silicon and copper together under nitrogen or as described in U.S. Pat. No. 2,380,996; or preferably by heating mixtures of copper oxides and silicon in the presence of hydrogen and/or hydrogen chloride (see, e.g., U.S. Pat. Nos. 4,314,908 and 2,380,997); or by heating copper salts (e.g., cuprous chloride) and silicon [see, e.g., Voorhoeve, et. al., J. Catalysis 4, 123 (1965)]. The use of copper formate as a catalyst is described in Lewis et al., "Selection of Copper Formate Catalysts for the Direct Synthesis of Methylchlorosilanes," K. M. Lewis and D. G. Rethwisch (Eds.), *Catalyzed Direct Reactions of Silicon*, published by Elsevier Science Publishers B. V., 1993. Activators other than copper are known in the art, but copper is greatly preferred. Once the proper form of the catalyst is chosen, the objective is the amount thereof that provides the best reaction results, followed by the selection of promoters combined with the catalyst that yields the best selectivity and best rates. This is a sliding scale type of selection and it ends when the most preferred results are obtained. For example, it is known that the amount of copper required to activate the silicon is usually less than about 10% by weight of the silicon used. Though trial and error, it has been found that, in general, an amount of from about 0.1 wt. %, preferably 0.5 wt. %, to about 5 wt. % of copper, basis weight of silicon, is regarded to be optimal. Good results are achievable at about 2 wt. % of copper by weight of the silicon used.

(4) Promoters There are variety of promoters that are employable to enhance the copper catalyzed reaction. As noted above in the prior art discussion, zinc and tin are frequently combined in promoting copper catalyzed silicon. Again, we see that the art has used a sliding scale process for selecting the preferred amount of zinc and tin to use. Lewis and Childress, U.S. Pat. No. 4,864,044 found that the effectiveness of copper as a catalyst can be dependent upon an effective amount of Zn promoter and a small concentration of tin. K. M. Lewis, et al., "Direct reactions of silicon with nanosized copper and copper compounds as catalyst precursors," supra, at Table 7, page 253, show the effects in a batch slurry phase direct synthesis reaction to make dimethyldichlorosilane, of varying the concentrations of copper, zinc and tin, and they readily achieved D/T ratios exceeding 20/1, which is a satisfactory ratio by commercial standards. Phosphorus has been employed in the direct reaction, and via the sliding scale process, the art has reported on improved selectivity when tin and zinc are also present. U.S. Pat. No. 4,762,940 describes the use of various phosphides such as copper phosphide to improve selectivity in the direct reaction. U.S. Pat. No. 4,898,960 reveals that phosphorus from quartz that was naturally high in phosphorus is a suitable promoter. According to The Lewis Report, page 4, "Apparently the use of any phosphorus compound that is not volatile, such as phosphides, leads to improved yield." Expanding on The Lewis Report, and of particular interest, is the use of the soluble copper phosphates as catalysts. In this respect, references made to Anderson et al., U.S. Pat. No. 6,580,000, who describe the use of cupric bis(diorganophosphate) as a catalyst/promoter in a direct reaction process. A preferred copper phosphorus salt is that of diethylphosphoric acid, to wit, $Cu((O)P(OC_2H_5)_2)_2$. U.S. Pat. No. 4,762,940 shows that metal arsenides and alloys of arsenic are used as promoters to enhance selectivity, overall yields of usable silanes, and silicon utilization. Also, disclosed is a composition comprising a direct reaction silicon/copper contact mass which includes arsenic as a component. All of such disclosures are relevant to the practice of this invention in respect to selection of materials for ascertaining optimization for the practice of this invention in accordance with the sliding scale process. In this respect, reference is made to Komitsky, et al., "THE INFLUENCE OF PROMOTER LEVELS ON THE DIRECT SYNTHESIS," at page 217-225 of *Silicon for the Chemical Industry IV*, Tromso, Norway, Jun. 3-5, 1998, Trondheim, Norway 2000 published by Norwegian University of Science and Technology, Trondheim, Norway): in particular to Tables 1 (page 220) and 2 (page 222), FIGS. 1 (page 219), 2 (page 221), and 3 (page 223), incorporated by reference herein, who demonstrate a manner of evaluation of copper, zinc, tin and phosphorus in obtaining high D/T selectivity a Rochow Process fluid bed process.

Other additives are well recognized in the art as having a demonstrably beneficial effect on the rate and selectivity of the direct reaction and they may also be employed in the practice of this invention. Notoriously well-known additives such as zinc powder, anhydrous $ZnCl_2$, ZnO and $ZnCO_3$ are obvious choices to be employed in the process of this invention. As Lewis and Kanner point out, cadmium salts, cobalt salts, antimony and bismuth salts are also suitable. These additives may be introduced at the silicon activation stage and/or during the reaction of the methyl bromide and dimethyl ether with the activated silicon particles. It is known in the art that these additives promote the formation of dimethylsilyl compounds. Consequently, their employment is expected to favor a high content of the desired cyclic dimethylsiloxanes oligomers. All of the foregoing has bearing on the practice of this invention because any of such combinations with copper catalyst as determined by the sliding scale process may prove to be more desirable than the combination of promoters described herein which achieve high D/T ratios.

The amount of the zinc additive employed may be about 0.01-0.5% by weight of the silicon charged to the reactor. In the preferred promoter system, Zn and Sn are used in combination, ranging from about an equal weight amount of each or a slight of one to the other, to a ratio of Zn to Sn of 100/1. The sliding scale process can be used to determine the optimum amount of each. An excellent combination for the methyl bromide reaction with Si is about a 0.1 weight % portion of each of Zn and Sn based on the weight of the Si in the reaction mass. That combination used with about 2 wt. % Cu metal, based on the weight of Si in the reaction mass is suitable for the processes of this invention. Such a catalyst/promoter system results in high dimethyldibromosilane selectivity in the range of 85% or greater, assuring a dimethylsiloxane productivity of at least 75 mole %, preferably at least 80 mole %, and most preferably at least 90 mole % of the methylsiloxanes produced. As a consequence, the dimethylsiloxane productivity ranges in a continuous operation over 85-90 mole per cent of the methylsiloxanes produced. With such a system, operation of the process in a solvent silicon metal slurry has the significant advantage of favoring up to 100 mole per cent conversion of the produced methyl siloxanes to cyclic dimethylsiloxane oligomer, however, in the typical case, some minor amount of methylsiloxane resin and some minor amount of end-capped fluid dimethylsiloxane are to be anticipated. In all such instances, the bed turnover exceeds one, the Si consumption exceeds 3.5 wt %/hour, generally exceeds 5 wt %/hour. If desired, selectivity may be enhanced by additions of small amounts of phosphorus and phosphorus compounds in line with concentrations of phosphorus recommended in the art. See Komitsky, et al., supra. In such a case, the sliding scale process may be use to determine what proportions and amounts are desirable. See Kim, et al. supra.

(5) The Reactants The reactants are silicon metal, discussed above, methyl bromide and dimethyl ether. According to the stoichiometry of the reaction to make a dimethylsilyl product (e.g., dimethyldibromosilane intermediate and dimethylsiloxanes), there is provided about 2 moles of methyl bromide to the reaction for every mole of dimethyl ether; however, in the reactor the amount should be less than this stoichiometric amount to avoid silicon bromide formation that fails to react with dimethyl ether. Consequently, the molar amount of dimethyl ether should exceed the stoichiometric amount dictated by the stoichiometry of the reaction, which means that the molar ratio of dimethyl ether to methyl bromide should be >0.5. There are practical processing limits that affect the amount of excess dimethyl ether from such stoichiometry one should choose, but two parameters stand out: one should choose a ratio that avoids the formation of silicon bromide products and minimizes the formation of methoxysilicon units to trace levels in the silicone products.

The reaction temperature for the reaction between the methyl bromide, silicon and dimethyl ether to yield the cyclic dimethylsiloxanes oligomers is that temperature at which the methyl bromide enters into reaction after the typical induction period. This constitutes the initiation of the in situ reaction discussed above. That reaction will occur above 200° C., typically at a temperature exceeding 240° C. According to the literature, the reaction can be carried out to a temperature as high as 400° C. However, in the typical operation of the process of this invention, the temperature of the reaction will range from, more preferably from about 280° C. to about 350° C. These temperatures are applicable irrespective of whether the process is carried out in a fluid bed or in a slurry suspension.

Fluidization Process Fluidization may be carried out according to the Lewis and Kanner patent, supra, and the Lewis and Childress patent, supra, utilizing standard operating conditions well understood by the art. Variation in the nature of the silicon metal particle distribution may be effected in accordance with the teachings of Freeburne, et al., supra.

Equilibration Though the process of this invention prefers making cyclic dimethylsiloxane oligomers, it is possible in the course of the reaction to have formed with the preferred oligomers, liquid linear poly(dimethylsiloxanes) oligomers containing up to 4-6 repeating units in sequence. It is preferred to equilibrate these liquid linear poly(dimethylsiloxanes) into the preferred cyclic dimethylsiloxanes oligomers and this can be easily accomplished by passing the linear fluids through an acid or basic bed, preferably an acid or basic ion exchange resin bed, most preferably a strong acid ion exchange resin bed. This technique is well known in the art. The preferred resins are the well-known sulphonic (sulfonic) acid ion exchange resins such as Nafion® perfluorosulfonic acid, the Amberlyst® sulfonic acid catalysts such as 15Dry, 35Dry and 36Dry, Dowex™ DR-2030, Dowex™ Monosphere DR-2030, Dowex™ G-26 (H), and one may employ an inorganic acid porous bed made of hydrochloric acid or sulfuric acid activated fuller's earth, and the like. Also preferred ion exchange resins are basic, especially the weak and strong basic ion exchange resins, such as Dowex™ Monosphere 550A and 700A, Dowex™ M-43, Amberlite IRA402Cl, Amberlite IRA410Cl, Amberlite IRA458 Cl, Amberlite IRA900 Cl, Amberlite IRA910 Cl, Amberjet 4400 Cl, Ambersep 900 OH, Ambersep 900 $SO_4$, Amberlite UP900, and the like.

The treatment is effected by passing the solution of dimethylsiloxanes products in inert liquid solvent, with or without suspended silicon, catalyst, promoter, and the like, through the bed at temperatures ranging from about room temperature up to the operational limits of the resin constituting the bed. Typically, the temperature ranges from about 60° C. to about 90° C.

There is the possibility that in the course of long term continuous operation of the slurry phase process of this invention, foaming can occur caused by gas buildup which might adversely affect the stability of the reaction and product separation. Should this occur, a sensible approach to resolving the issue would be to employ the antifoaming regimen described by Mendicino et al., U.S. Pat. No. 5,783,720, at column 8, line 1 to column 10, line 63, which is incorporate herein by reference, or the use of FS 1265 (Dow Corning® FS 1265 Fluid, 10,000 CST.), as described by K. M. Lewis, et al., "Direct reactions of silicon with nanosized copper and copper compounds as catalyst precursors," Silicon for the Chemical Industry VI, pages 243-263, particularly page 247, Loen, Norway, Jun. 17-21, 2002, Norwegian University of Science and Technology, Trondheim, Norway, which regimen is incorporated by reference herein.

The slurry phase and fluid bed phase processes can be carried out at subatmospheric to superatmospheric pressures, but most conveniently is carried out at atmospheric pressure. The system can be maintained dry, i.e., essentially free of water, by feeding and maintaining a constant inert gas atmosphere within the system, such as dry nitrogen gas. It is not desirable to bring or allow water or oxygen into the system, especially the reaction, and therefore it is desirable that the components of the reaction be kept the essentially free of water and oxygen that adversely affects the process.

DETAILED DESCRIPTION OF THE DRAWING AND PROCESS OPERATION

Figure 2:
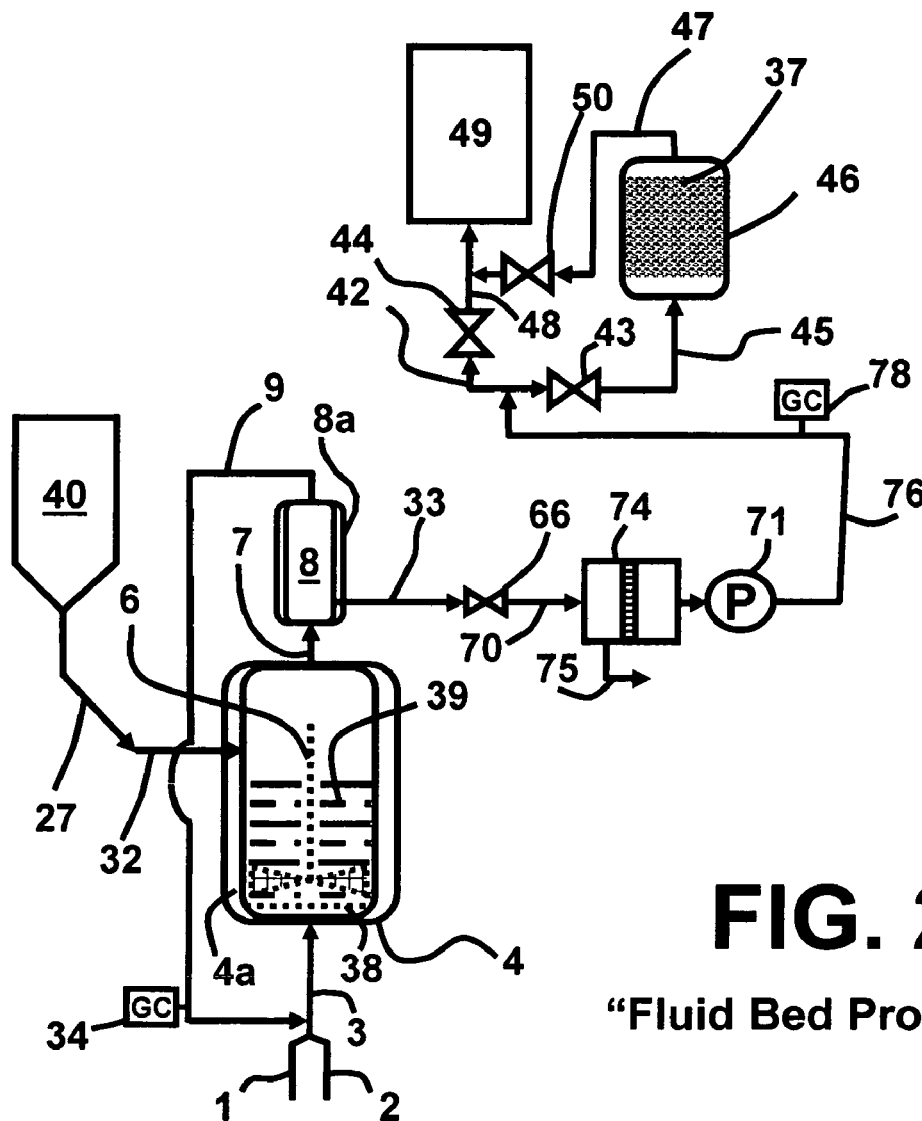
FIG. 2 depicts schematically a plan view of apparatus and material flow for practicing a fluid bed version of the process of this invention and producing the dimethylsiloxane compositions of this invention. As is the case for FIG. 1, FIG. 2 relates to the use of conventional equipment employed in the chemical industry to provide the advantages herein described for the process of this invention.

FIGS. 1 and 2 illustrate the fundamental simplicity of the slurry and fluid bed phase processes of this invention compared to the standard Rochow process containing stages I through V (1 through 5) discussed above. In this respect, reference is made to FIG. 2 flow diagram of Brinson, footnote 6 supra and to FIGS. 4 and 5 of Kanner and Lewis, "Commercial Production of Silanes by the Direct Synthesis," supra.

FIG. 1 characterizes a slurry process operation. Line 1 provides feed of methyl bromide to reaction vessel 4 and line 2 provides feed of dimethyl ether, both gases since they both boil below 0° C., to reaction vessel 4. Lines 1 and 2, as well as recycle gas lines 9, merge into line 3, which feeds the dimethyl ether and methyl bromide as a gaseous mixture into the bottom of reaction vessel 4. A liquid suspension stream containing, e.g., one part direct synthesis quality silicon/copper catalyst/promoter and 2 parts solvent, all by weight, is continuously fed via line 32. Indeed, the initial feed of suspension to the reaction vessel may be fed via line 32. The inert solvent is initially supplied, or periodically recycled from the reaction vessel 4 after suitable cleanup to remove methyl silicone resin (as describe above), and fed via line 25 to replenishment vessel 30 to which is supplied the silicon/copper catalyst/promoter under nitrogen gas atmosphere that is separately prepared. A suitable silicon/copper catalyst/promoter composition for this operation is an heat activated (2 hours fluidization in $N_2$ at 325-350° C.) 210 g of technical grade silicon (98.5 wt % Si minimum, 0.20-0.4 wt. % Al, 0.3-0.6 wt. % Fe) to 5.0 g copper catalyst containing 0.1 g each of Zn and Sn, made according to Example 1N (as described at column 19, starting at lines 57 through to column 21, line 42) of Lewis and Childress, U.S. Pat. No. 4,864,044, incorporated herein by reference, supra. Sufficient amount of the inert liquid solvent may be used as an aid in delivering the suitable silicon/copper catalyst/promoter composition by way of line 29 to replenishment vessel 30. A suspension composition is formed in vessel 30 and it is transported with aid from pump 31 to line 32. Line 32 may be or contain a Kenics® KM Static mixer to aid in uniform distribution of the suspension prior to feeding to the reactions zone. The choice of solvent will dictate the operating conditions. For example, a suitable solvent is dodecylbenzene, in which case the reactor is stirred and heated to 325° C. The dimethyl ether and methyl bromide gases are conveyed from commercially supplied cylinders through beds of commercial grade Drierite, a drying agent (anhydrous calcium sulfate). Line 3 may comprise a laminar flow or low Reynolds Number static mixer to enhance blending of the feeds from lines 1, 2 and 9.

Reaction vessel 4 may be a tank or tubular continuous, stirred (agitated) chemical reactor. Reaction vessel 4 is preferably provided with heat jacketing 4a with temperature controls to achieve and maintain the inert liquid at the desired reaction temperature. Stirring may be achieved by incorporating static mixer design into the reactor or by incorporating impellers within the reactor. In this case, it is characterized as a stirred tank reactor, indicated by stirrer 6, shown with a single double bladed impeller but which may contain multiple impeller units lined along the length of the stirrer's shaft, from the depth of liquid suspension 5 therein to below its surface. A Chemineer® reactor such as the 5.8 liter version described by Mendicino et al., U.S. Pat. No. 5,783,720, at column 15, lines 19-29, represents a suitable laboratory reactor for carrying out this process. Stationary wall baffles sized to clear impeller movement present in the reactor 4 aids mixing of the reactor's reaction ingredients. The liquid suspension 5 within reaction vessel 4 contains inter alia the higher boiling inert liquid (e.g., dodecylbenzene), methyl bromide, dimethyl ether, suspended copper catalyzed activated silicon and other promoters, and cyclic siloxane oligomers. Silicon may be activated in situ within the reactor as characterized in U.S. Pat. No. 3,775,457, supra, or pre-activated according to Example 1 of Lewis and Childress, supra.

After the typical induction period, reaction takes place and vapors from the reaction zone above the slurry within reaction vessel 4 are typically methyl bromide, unreacted dimethyl ether, and entrained methylsiloxanes product such as cyclic dimethylsiloxane oligomers. The vapors are passed via lines 7 into simple separation column 8. Separation column 8 is a simple distillation column of no more than about 5 to 10 theoretical plates in design. It is desirable to provide cooling jacket 8a about column 8 to aid in separation of the methyl bromide and dimethyl ether from the cyclic dimethylsiloxane oligomers formed in reactor 4. Methyl bromide and dimethyl ether have boiling points below 0° C. while the lowest boiling siloxane product boils above 50° C. so that a relatively modest distillation column is sufficient. Condensation product formed in separation column 8 is removed via line 33 and with the aid of pump 26, is passed to line 41 where it is subject to a gas chromatographic [GC 78] analysis to determine amount of linear poly(dimethylsiloxane) oligomers in the product stream. The gases, methyl bromide and dimethyl ether, are recycled through line 9 to line 3 and are analyzed by GC analyzer 34 so as to maintain the selected methyl bromide/dimethyl ether molar ratio, which in this illustration is 1.5. The molar ratio of 1.5 is maintained by addition of appropriate amounts of either component through lines 1 and 2 noted above. [See: Rotzsche et al., "Gas Chromatographic Analysis in the Manufacture of Chlorosilanes," page 207 et seq., K. M. Lewis and D. J. Rethwisch (Eds.), *Catalyzed Direct Reactions of Silicon*, published by Elsevier Science Publishers. B. V., 1993]

However, by using a higher boiling inert solvent the liquid suspension 5 may be maintained at a higher temperature than is contemplated above. For example, Therminol® 72 heat transfer fluid, which has an operating range of from −10° C. to 380° C. (15° F. to 720° F.) [http://www.therminol.com/pages/products/72.asp], may substituted for the dodecylbenzene inert liquid solvent and this will allow for a higher reaction temperature reaction using the same reaction mixture and proportions. To take advantage of the inherent reaction stability of the reaction mixture in Therminol® 72, the temperature of liquid suspension 5 is raised to 350° C. to create a higher reaction rate and increased productivity. As a result, the upper surface of liquid suspension 5 is made more turbulent because of the consequent increase in gas flow in reaction vessel 4. Because of this increase flow, a greater reflux is created at the surface of suspension 5. The increase in temperature increases the rate of formation of cyclic dimethylsiloxane oligomer in suspension 5. Because of this increase in gas flow from reaction vessel 4 via line 7 to separation column 8, cooling jacket 8a about the column may be used to aid in separation and insure constant separation of the cyclic dimethylsiloxane oligomers product. Suspension 5, rich in cyclic dimethylsiloxane oligomer is continuously removed by way of line 33 as stated above and subjected to GC analysis. In case of foaming occurring in column 8, one may introduce anti-foaming aids as discussed previously.

The volatile dimethylsiloxane components in line 41 are passed to line 42. If the volatile dimethylsiloxane component is sufficiently rich in cyclic dimethylsiloxane oligomers for subsequent and conventional silicones operations, then valves 43 and 50 are closed and valve 44 is opened, and the product is passed to collection tank 49 for subsequent usage. However, if the dimethylsiloxane components have a linear dimethylsiloxane oligomer content that is greater than is regarded to be satisfactory, then valve 44 is closed and valves 43 and 50 are opened, to allow the flow of the stream by way of line 45 to depolymerization vessel 46 containing an ion exchange resin bed 37. In this case, the preferred resin bed of Nafion is employed. The linear dimethylsiloxanes are converted to cyclic dimethylsiloxane oligomers and the overhead line 47 passes the depolymerized stream to valve 50 and thence to line 48 to collection tank 49.

Occasionally, the inert liquid solvent used in suspension 5 will reach a level of methylsilicone resin formation that will require its replenishment with fresh solvent. This can be carried out by shutting down the process and removing solvent from the reaction vessel 4, where cleanup of the solvent is effected by removing the methylsilicone resin as previously described. However, solvent suspension can be removed by a side arm pipe connection to reaction vessel 4, not shown, with clean up separate from vessel 4, while at that time introducing additional solid silicon/catalyst/promoter as described above.

FIG. 2 illustrates a fluid bed process to make dimethylsiloxane oligomers directly by the reaction of methyl bromide, dimethyl ether in a fluidized bed of silicon particle within which there are provided copper catalyst and promoters, such as Zn and Sn, as described in supra. Separately prepared activated silicon/catalyst/promoter, made as set forth above (not shown) is provided in hopper vessel 40 from which it is supplied to line 27, then to line 32 (as afore-described) where it is introduced to reaction vessel 4, provided with heat jacketing 4a, as a solids stream of fluidizable particles to form fluid bed 39. In the case of FIG. 2, where reaction vessel 4 is used for fluidization, a gas/vapor distribution screen or plate 38 is employed to establish a manifold below it, to provide a space at the bottom of reaction vessel 4 to allow distribution of the gas/vapor reactants from line 3 within the manifold and insure uniform distribution of gas through the fluidized bed 39 to establish and maintain fluidization. Because of the different nature of the fluidized reaction bed from the slurry, feed line 32 is situated above the top of fluidized bed 39. The reaction conditions within reaction vessel 4 are essential equivalent to the operation of the solvent slurry process of FIG. 1 in terms of methyl bromide, dimethyl ether, silicon metal/catalyst/promoter, temperature and pressure.

Lines 1, 2, 3, analyzer 34 and 9 operate in FIG. 2 as described above with respect to FIG. 1. The fluidized bed components initially supplied, or periodically recycled from the reaction vessel 4 after suitable cleanup to remove methyl silicone resin (as describe above), is fed to hopper 40 to which is also supplied the activated silicon/copper catalyst/promoter under nitrogen gas atmosphere that is separately prepared. The fluid bed operation is as describe by Lewis and Childress, U.S. Pat. No. 4,864,044, supra. The dimethyl ether and methyl bromide gases are conveyed from commercially supplied cylinders through beds of commercial grade Drierite, a drying agent (anhydrous calcium sulfate). Line 3 may comprise a laminar flow or low Reynolds Number static mixer to enhance blending of the feeds from lines 1, 2 and 9.

Reaction vessel 4 is preferably provided, through heat jacketing 4a, with temperature controls to achieve and maintain the fluid bed at the desired reaction temperature. A stirred fluid bed 39 may be achieved by incorporating static mixer design into the reactor or by incorporating impellers within the reactor. In this case, it is characterized as a stirred fluid bed, indicated by stirrer 6, shown with a single double bladed impeller but which may contain multiple impeller units lined along the length of the stirrer's shaft, from the depth of bed 39 therein to just below its surface. Silicon may be activated in situ within the reactor as characterized in U.S. Pat. No. 3,775,457, supra, or pre-activated according to Example 1 of Lewis and Childress, supra. Pre-activation is preferred.

After the typical induction period, reaction takes place and vapors from the reaction zone above the bed within reaction vessel 4 are typically methyl bromide, unreacted dimethyl ether, and entrained methylsiloxanes product such as cyclic dimethylsiloxane oligomers, plus elutriated fine solid bed particles. The vapors are passed via lines 7 into separation column 8. Separation column 8 and jacketing 8a function as described with respect to the solvent slurry process of FIG. 1. Methyl bromide and dimethyl ether have boiling points below 0° C. while the lowest boiling siloxane product boils above 50° C. so that a relatively modest distillation column is sufficient. Condensation product formed in separation column 8 is removed via line 33, through flow control valve 66 passed through line 70 with the aid of pump 71 into filter vessel 74. Filter vessel 74 may comprise one of more filter systems such as one or more cartridge or standard filters alone or in series, or in combination with a cyclone filter or a series of cyclone filters, or a series of cyclone filters alone. Spent and waste solids are removed from the liquid condensation product by way of line 75 for treatment and/or disposal (not shown). The effluent liquid from filter vessel 74 with the aid of pump 71, is passed to line 76 where it is subject to a gas chromatographic [GC 78] analysis to determine amount of linear poly(dimethylsiloxane) oligomers in the product stream. The gases, methyl bromide and dimethyl ether, are recycled through line 9 to line 3 and are analyzed by GC analyzer 34 so as to maintain the selected methyl bromide/dimethyl ether molar ratio, which in this illustration is 1.5. The molar ratio of 1.5 is maintained by addition of appropriate amounts of either component through lines 1 and 2 noted above. [See: Rotzsche et al., "Gas Chromatographic Analysis in the Manufacture of Chlorosilanes," page 207 et seq., K. M. Lewis and D. J. Rethwisch (Eds.), *Catalyzed Direct Reactions of Silicon*, published by Elsevier Science Publishers. B. V., 1993]

After the analysis by GC analyzer 78, the liquid effluent in line 76 is passed to line 42, and the stream is thereafter handled according to the description set forth in supra and cyclic dimethylsiloxane oligomer product is stored in collection tank 49.

Preparation of Cyclic Dimethylsiloxanes in a Fluidized Bed Reactor: Activation of a silicon contact mass: grind together under $N_2$ 4 g. of copper powder, 0.2 g. of ZnO and 0.2 g. of Sn powder in a mortar for a few minutes; then add to this grind under $N_2$ 10 g. of (65×150 mesh) silicon [98.5 wt % Si, 0.2-0.5 wt % Fe, 0.3-0.5 wt % Al, 0.3 wt % Ca], and continue grinding until uniform; add under $N_2$ additional 190 g. of the Si powder with thorough mixing; transfer the silicon contact mass mixture under $N_2$ to a fluidized bed reactor similar to that described at col. 8, from line 59 to col. 9, ending at line 14, of the Lewis and Kanner patent, U.S. Pat. No. 4,593,114; activate the silicon contact mass mixture by heating it to 350° C. for 2 hours while it is fluidized by nitrogen; and cool the activated mass to room temperature under nitrogen.

Fluidize the mass again at 325° C. with nitrogen. Change the feed gas to a mixture of 0.5 standard liter/minute of methyl bromide and 0.34 standard liter/minute of dimethyl ether or a mole ratio of $CH_3Br/CH_3OCH_3$ of 1.48. Carry out the reaction for a total of 26 hours (not including overnight shutdowns). A reaction rate of silicon during this time will range about 3.5% to 7%/hr. Add 10 g. of activated silicon contact mass each hour. Collect product during this period and analyze by GC. Repeated runs at the above conditions, each for more than 20 hrs, will contain at least 80% and more generally 90% to 95% of $D_3$ to $D_7$ dimethylsiloxane cyclics based on the silicon consumed along with relatively small amounts of trimethylsiloxy and methoxy end-blocked linear dimethylsiloxanes.

Preparation of Cyclic Dimethylsiloxanes as a Stirred Slurry in Solvent: Add 200 g. of the activated silicon contact mass mixture described above under nitrogen to a 2.0 liter, 130 mm wide glass reactor fitted with an electric heating mantle controlled by a digital heater/temperature controller and provided with a digital speed-control powered 29.3 cm. vertical stirrer shaft (centrally located in the reactor) containing two 6 cm.-separated, curved pitched-5.715 cm. diameter glass 6-bladed impellers attached at the bottom of the shaft.

Slurry the mixture with an equal volume of SASOL 7050, supra, in the glass reactor. Feed a dried gas mixture of methyl bromide at 0.6 standard liter/minute and 0.4 standard liter of dimethyl ether representing a molar ratio of $CH_3Br/(CH_3)_2O$ of 1.5 continuously to the stirred slurried mixture of the solvent and activated Si mass while maintaining it at the reaction temperature of 325° C. Run the reaction, similar to the previous example, for a total of 24 hours, not including overnight shutdowns. Add about 5% of additional activated silicon mass each hour. A conversion rate of silicon during this time is achieved at about 5%/hr.

Repeated runs, each for more than 20 hrs at the above conditions, lead to product collected that contain at least 80% and more generally 90% to 95% of $D_3$ to $D_7$ dimethylsiloxane cyclics based on the silicon consumed. Dimethylsiloxane linears in the product is less than 10% thereof.

Though this invention has been described with references to details in the selection of materials, process sequencing, preferred methods and materials, it is not intended that this invention should be so limited from the obvious breadth and scope thereof.

The invention claimed is:

1. A continuous process for making cyclic dimethylsiloxane oligomers which comprises continuously feeding a mixture of methyl bromide and dimethyl ether within a direct reaction zone containing a dynamic bed of activated direct synthesis quality silicon metal particles associated with direct synthesis quality copper catalyst and promoter at an elevated temperature between 200° C. and 400° C., which bed is rendered dynamic by either gas fluidization or by stirring in the form of a slurry in an inert liquid solvent having a boiling point greater than said elevated temperature, to effect a reaction between the methyl bromide, dimethyl ether and silicon to produce cyclic dimethylsiloxane oligomers such that there is at least one complete silicon metal bed turnover during the continuous process, and the proportion of dimethylsiloxanes inclusive of cyclic dimethylsiloxane oligomers produced in said bed is greater than 75 mole % of the methylsiloxanes produced from said reaction, continuously recovering dimethylsiloxanes inclusive of such cyclic dimethylsiloxane oligomers from the direct reaction zone, and recycling methyl bromide as formed in the direct reaction zone to the feed of such mixture.

2. The continuous process of claim 1 wherein the bed is agitated by gas fluidization.

3. The continuous process of claim 1 wherein the bed is agitated as a slurry in an inert liquid solvent.

4. The continuous process of claim 2 where the catalyst is metallic copper, soluble or insoluble copper compounds in an amount less than about 10 weight %, basis weight of silicon and the promoter comprises a combination of zinc and tin compounds.

5. The continuous process of claim 3 where the catalyst is metallic copper, soluble or insoluble copper compounds in an amount less than about 10 weight %, basis weight of silicon and the promoter comprises a combination of zinc and tin compounds.

6. The continuous process of claim 4 where the catalyst is metallic copper, soluble or insoluble copper compounds in an amount from about 0.1 wt. % to about 5 wt. % of copper, basis weight of silicon, and the promoter comprises a combination of zinc and tin compounds.

7. The continuous process of claim 4 where the catalyst is metallic copper, soluble or insoluble copper compounds in an amount from about 0.1 wt. % to about 5 wt. % of copper, basis weight of silicon, and the promoter comprises a combination of zinc and tin compounds.

8. The continuous process of claim 2 wherein the major portion of the dimethylsiloxanes produced in the bed is cyclic dimethylsiloxane oligomers.

9. The continuous process of claim 3 wherein the major portion of the dimethylsiloxanes produced in the bed is cyclic dimethylsiloxane oligomers.

10. The continuous process of claim 1 wherein the proportion of such dimethylsiloxanes produced in said bed is greater than 80 mole % of the methylsiloxanes produced from said reaction.

11. The continuous process of claim 10 wherein the proportion of such dimethylsiloxanes produced in said bed is greater than 90 mole % of the methylsiloxanes produced from said reaction.

12. The continuous process of claim 9 where, in using an agitated inert solvent slurried bed, essentially all of the dimethylsiloxanes is cyclic dimethylsiloxane oligomers.

13. The continuous process of claim 3 which has a bed turnover rate that exceeds 3.5% silicon per hour.

14. The continuous processes of claim 3 wherein cyclic dimethylsiloxane oligomers dissolved in the inert liquid is at a concentration greater, on a percent by weight basis, than any other dimethyl siloxane component present in said inert liquid.

15. The continuous process of claim 14 wherein the temperature is from about 240° C. to about 350° C.

16. The continuous process of claim 15 wherein the process is carried out at atmospheric pressure.

17. The continuous process of claim 1 wherein the products of the reaction are subjected to depolymerization of residual linear dimethyl siloxane oligomers to cyclic dimethylsiloxane oligomers.

18. The continuous process of claim 4 wherein the zinc and tin promoter content in the reaction zone are each from about 0.005 to about 1 weight % of the silicon metal in the bed.

19. The continuous process of claim 5 wherein the zinc and tin promoter contents in the reaction zone are each from about 0.005 to about 1 weight % of the silicon metal in the bed.

20. The continuous process of claim 19 wherein the zinc and tin promoter are each present in essentially the same weight %.

21. The continuous process of claim 20 wherein the zinc and tin promoter are each present in about 0.1 weight %.

22. The continuous process of claim 19 wherein the copper catalyst content is from about 0.1 wt. % to about 5 wt. % of copper, basis weight of silicon.

23. The continuous process of claim 20 wherein the copper catalyst content is from about 0.1 wt. % to about 5 wt. % of copper, basis weight of silicon.

24. The continuous process of claim 23 wherein the copper catalyst content is from about 0.5 wt. % to about 5 wt. % of copper, basis weight of silicon.

25. The continuous process of claim 23 wherein the copper catalyst content is from about 0.5 wt. % to about 5 wt. % of copper, basis weight of silicon.

* * * * *